United States Patent
Miller

(10) Patent No.: US 9,433,400 B2
(45) Date of Patent: Sep. 6, 2016

(54) MANUAL INTRAOSSEOUS DEVICE

(75) Inventor: Larry J. Miller, Spring Branch, TX (US)

(73) Assignee: Vidacare LLC, Wayne, PA (US)

(*) Notice: Subject to any disclaimer, the term of this patent is extended or adjusted under 35 U.S.C. 154(b) by 1203 days.

(21) Appl. No.: 12/787,228

(22) Filed: May 25, 2010

(65) Prior Publication Data
US 2010/0298784 A1  Nov. 25, 2010

Related U.S. Application Data

(62) Division of application No. 11/042,912, filed on Jan. 25, 2005, now Pat. No. 8,641,715.

(60) Provisional application No. 60/539,171, filed on Jan. 26, 2004, provisional application No. 60/547,868, filed on Feb. 26, 2004.

(51) Int. Cl.
*A61B 17/34* (2006.01)
*A61B 10/02* (2006.01)
*A61B 17/92* (2006.01)

(52) U.S. Cl.
CPC ............. *A61B 10/025* (2013.01); *A61B 17/34* (2013.01); *A61B 17/3472* (2013.01); *A61B 17/3476* (2013.01); *A61B 2010/0258* (2013.01); *A61B 2017/348* (2013.01); *A61B 2017/3492* (2013.01); *A61B 2017/925* (2013.01)

(58) Field of Classification Search
CPC ............ A61B 10/025; A61B 2010/0258; A61B 17/34; A61B 17/3472; A61B 17/3476; A61B 2017/348; A61B 2017/3492
USPC ............ 606/79, 80, 86 R, 167, 185
See application file for complete search history.

(56) References Cited

U.S. PATENT DOCUMENTS

| | | | |
|---|---|---|---|
| 1,539,637 A | 5/1925 | Bronner et al. | |
| 2,138,842 A | 12/1938 | Drew et al. | |
| 2,261,958 A | 11/1941 | Burn et al. | |
| 2,317,648 A | 4/1943 | Siqveland | 32/26 |
| 2,419,045 A | 4/1947 | Whittaker | 128/305 |
| 2,773,501 A | 12/1956 | Young | 128/221 |
| 2,860,635 A | 11/1958 | Wilburn et al. | |
| 3,104,448 A | 9/1963 | Morrow et al. | |
| 3,120,845 A | 2/1964 | Horner | 128/310 |
| 3,173,417 A | 3/1965 | Homer | 128/305 |

(Continued)

FOREIGN PATENT DOCUMENTS

| | | | |
|---|---|---|---|
| CA | 2138842 A1 | 6/1996 | |
| CA | 2 454 600 | 1/2004 | A61B 10/00 |

(Continued)

OTHER PUBLICATIONS

International Preliminary Report on Patentability, PCT/US2007/072202, 10 pages, Mailed Jan. 15, 2009.

(Continued)

*Primary Examiner* — Larry E Waggle, Jr.
(74) *Attorney, Agent, or Firm* — Baker & Hostetler LLP

(57) ABSTRACT

An apparatus for penetrating the bone marrow of a bone is provided. The apparatus includes a handle having a drive shaft, a connector having a first end operable to connect to a drive shaft and a second end operable to connect to a penetrator hub and a penetrator hub having a penetrator that accesses the bone marrow.

9 Claims, 8 Drawing Sheets

(56) References Cited

U.S. PATENT DOCUMENTS

| | | | | |
|---|---|---|---|---|
| 3,175,554 | A | 3/1965 | Stewart | 128/2 |
| 3,507,276 | A | 4/1970 | Burgess et al. | 128/173 |
| 3,543,966 | A | 12/1970 | Ryan et al. | 222/94 |
| 3,815,605 | A | 6/1974 | Schmidt et al. | 128/305 |
| 3,835,860 | A | 9/1974 | Garretson | 128/310 |
| 3,893,445 | A | 7/1975 | Hofsess | 128/2 |
| 3,991,765 | A | 11/1976 | Cohen | 128/305 |
| 4,021,920 | A | 5/1977 | Kirschner et al. | 32/28 |
| 4,099,518 | A | 7/1978 | Baylis et al. | 600/567 |
| 4,124,026 | A | 11/1978 | Berner et al. | 128/303 R |
| 4,142,517 | A * | 3/1979 | Stavropoulos et al. | 600/567 |
| 4,170,993 | A | 10/1979 | Alvarez | 128/214 R |
| 4,185,619 | A | 1/1980 | Reiss | 128/1.1 |
| 4,194,505 | A | 3/1980 | Schmitz | 128/218 |
| 4,258,722 | A * | 3/1981 | Sessions | A61B 10/025 600/566 |
| 4,262,676 | A | 4/1981 | Jamshidi | 128/753 |
| 4,306,570 | A | 12/1981 | Matthews | 128/754 |
| 4,333,459 | A | 6/1982 | Becker | 128/218 F |
| 4,381,777 | A | 5/1983 | Garnier | 604/188 |
| 4,441,563 | A | 4/1984 | Walton, II | 173/163 |
| 4,469,109 | A | 9/1984 | Mehl | 128/753 |
| 4,484,577 | A | 11/1984 | Sackner et al. | 128/203.28 |
| 4,543,966 | A | 10/1985 | Islam et al. | 128/754 |
| 4,553,539 | A | 11/1985 | Morris | 128/132 D |
| 4,605,011 | A | 8/1986 | Naslund | 128/752 |
| 4,620,539 | A | 11/1986 | Andrews et al. | 128/303 |
| 4,630,616 | A * | 12/1986 | Tretinyak | 600/566 |
| 4,646,731 | A | 3/1987 | Brower | 128/156 |
| 4,654,492 | A | 3/1987 | Koerner et al. | 200/153 P |
| 4,655,226 | A | 4/1987 | Lee | 128/754 |
| 4,659,329 | A | 4/1987 | Annis | 604/180 |
| 4,692,073 | A | 9/1987 | Martindell | 408/239 A |
| 4,711,636 | A | 12/1987 | Bierman | 604/180 |
| 4,713,061 | A | 12/1987 | Tarello et al. | 604/200 |
| 4,716,901 | A | 1/1988 | Jackson et al. | 128/343 |
| 4,762,118 | A | 8/1988 | Lia et al. | 128/4 |
| 4,772,261 | A | 9/1988 | Von Hoff et al. | 604/51 |
| 4,787,893 | A | 11/1988 | Villette | 604/188 |
| 4,793,363 | A | 12/1988 | Ausherman et al. | 128/754 |
| 4,812,008 | A | 3/1989 | Tokumaru et al. | |
| 4,867,158 | A | 9/1989 | Sugg | 128/305.1 |
| 4,919,146 | A | 4/1990 | Rhinehart et al. | 128/752 |
| 4,921,013 | A | 5/1990 | Spalink et al. | 137/614.05 |
| 4,935,010 | A | 6/1990 | Cox et al. | 604/122 |
| 4,940,459 | A | 7/1990 | Noce | 604/98 |
| 4,944,677 | A | 7/1990 | Alexandre | 433/165 |
| 4,969,870 | A | 11/1990 | Kramer et al. | 604/51 |
| 5,002,546 | A | 3/1991 | Romano | 606/80 |
| 5,025,797 | A | 6/1991 | Baran | 128/753 |
| 5,036,860 | A | 8/1991 | Leigh et al. | 128/754 |
| 5,057,085 | A | 10/1991 | Kopans | 604/173 |
| 5,074,311 | A | 12/1991 | Hasson | 128/754 |
| 5,116,324 | A | 5/1992 | Brierley et al. | 604/180 |
| 5,120,312 | A | 6/1992 | Wigness et al. | 604/175 |
| 5,122,114 | A | 6/1992 | Miller et al. | 604/49 |
| 5,137,518 | A | 8/1992 | Mersch | 604/168 |
| 5,139,500 | A | 8/1992 | Schwartz | 606/96 |
| RE34,056 | E | 9/1992 | Lindgren et al. | 128/754 |
| 5,172,701 | A | 12/1992 | Leigh | 128/753 |
| 5,172,702 | A | 12/1992 | Leigh et al. | 128/754 |
| 5,176,415 | A | 1/1993 | Choksi | |
| 5,176,643 | A | 1/1993 | Kramer et al. | 604/135 |
| 5,195,985 | A | 3/1993 | Hall | 604/195 |
| 5,203,056 | A | 4/1993 | Funk et al. | 24/543 |
| 5,207,697 | A | 5/1993 | Carusillo et al. | 606/167 |
| 5,249,583 | A | 10/1993 | Mallaby | 128/754 |
| 5,257,632 | A | 11/1993 | Turkel et al. | 128/754 |
| 5,261,877 | A | 11/1993 | Fine et al. | |
| 5,269,785 | A | 12/1993 | Bonutti | 606/80 |
| 5,279,306 | A | 1/1994 | Mehl | 128/753 |
| 5,312,364 | A | 5/1994 | Jacobs | 604/180 |
| 5,324,300 | A | 6/1994 | Elias et al. | 606/180 |
| 5,332,398 | A | 7/1994 | Miller et al. | 604/175 |
| 5,333,790 | A | 8/1994 | Christopher | 239/391 |
| 5,341,823 | A | 8/1994 | Manosalva et al. | 128/898 |
| 5,348,022 | A | 9/1994 | Leigh et al. | 128/753 |
| 5,357,974 | A | 10/1994 | Baldridge | 128/754 |
| 5,368,046 | A | 11/1994 | Scarfone et al. | 128/754 |
| 5,372,583 | A | 12/1994 | Roberts et al. | 604/51 |
| 5,383,859 | A | 1/1995 | Sewell, Jr. | 604/164 |
| 5,385,553 | A | 1/1995 | Hart et al. | 604/167 |
| 5,400,798 | A | 3/1995 | Baran | 128/754 |
| 5,405,348 | A | 4/1995 | Anspach et al. | 606/80 |
| 5,423,824 | A | 6/1995 | Akerfeldt et al. | 606/80 |
| 5,431,655 | A | 7/1995 | Melker et al. | 606/79 |
| 5,451,210 | A | 9/1995 | Kramer et al. | 604/137 |
| 5,484,442 | A | 1/1996 | Melker et al. | 606/79 |
| D369,858 | S | 5/1996 | Baker et al. | D24/112 |
| 5,526,821 | A | 6/1996 | Jamshidi | 128/753 |
| 5,529,580 | A | 6/1996 | Kusunoki et al. | 606/170 |
| 5,549,565 | A | 8/1996 | Ryan et al. | 604/167 |
| 5,554,154 | A | 9/1996 | Rosenberg | 606/80 |
| 5,556,399 | A | 9/1996 | Huebner | 606/80 |
| 5,558,737 | A | 9/1996 | Brown et al. | 156/172 |
| 5,571,133 | A | 11/1996 | Yoon | |
| 5,586,847 | A | 12/1996 | Mattern et al. | 408/239 A |
| 5,591,188 | A | 1/1997 | Waisman | 606/182 |
| 5,595,186 | A | 1/1997 | Rubinstein et al. | 128/754 |
| 5,601,559 | A | 2/1997 | Melker et al. | 606/79 |
| 5,632,747 | A | 5/1997 | Scarborough et al. | 606/79 |
| 5,672,155 | A | 9/1997 | Riley et al. | |
| 5,713,368 | A | 2/1998 | Leigh | 128/753 |
| 5,724,873 | A | 3/1998 | Hillinger | 81/451 |
| 5,733,262 | A | 3/1998 | Paul | 604/116 |
| 5,752,923 | A | 5/1998 | Terwilliger | 600/562 |
| 5,762,639 | A | 6/1998 | Gibbs | 604/272 |
| 5,766,221 | A | 6/1998 | Benderev et al. | 606/232 |
| 5,769,086 | A | 6/1998 | Ritchart et al. | 128/753 |
| 5,779,708 | A | 7/1998 | Wu | 606/80 |
| 5,800,389 | A | 9/1998 | Burney et al. | 604/93 |
| 5,807,277 | A | 9/1998 | Swaim | 600/567 |
| 5,810,826 | A | 9/1998 | Akerfeldt et al. | 606/80 |
| 5,817,052 | A | 10/1998 | Johnson et al. | 604/51 |
| 5,823,970 | A | 10/1998 | Terwilliger | 600/564 |
| D403,405 | S | 12/1998 | Terwilliger | D24/130 |
| 5,858,005 | A | 1/1999 | Kriesel | 604/180 |
| 5,865,711 | A | 2/1999 | Chen | 604/136 |
| 5,868,711 | A | 2/1999 | Kramer et al. | 604/136 |
| 5,868,750 | A | 2/1999 | Schultz | 606/104 |
| 5,873,510 | A | 2/1999 | Hirai et al. | 227/130 |
| 5,885,226 | A | 3/1999 | Rubinstein et al. | 600/564 |
| 5,891,085 | A | 4/1999 | Lilley et al. | 604/68 |
| 5,911,701 | A | 6/1999 | Miller et al. | 604/22 |
| 5,911,708 | A | 6/1999 | Teirstein | 604/183 |
| 5,916,229 | A | 6/1999 | Evans | 606/171 |
| 5,919,172 | A | 7/1999 | Golba, Jr. | 604/272 |
| 5,924,864 | A | 7/1999 | Loge et al. | 433/118 |
| 5,927,976 | A | 7/1999 | Wu | 433/82 |
| 5,928,238 | A | 7/1999 | Scarborough et al. | 606/79 |
| 5,941,706 | A | 8/1999 | Ura | 433/165 |
| 5,941,851 | A | 8/1999 | Coffey et al. | 604/131 |
| 5,951,026 | A | 9/1999 | Harman, Jr. et al. | |
| 5,960,797 | A | 10/1999 | Kramer et al. | 128/899 |
| 5,980,545 | A | 11/1999 | Pacala et al. | 606/170 |
| 5,993,417 | A | 11/1999 | Yerfino et al. | 604/110 |
| 5,993,454 | A | 11/1999 | Longo | 606/80 |
| 6,007,496 | A | 12/1999 | Brannon | 600/565 |
| 6,017,348 | A | 1/2000 | Hart et al. | 606/79 |
| 6,018,094 | A | 1/2000 | Fox | 623/11 |
| 6,022,324 | A | 2/2000 | Skinner | 600/566 |
| 6,027,458 | A | 2/2000 | Janssens | 600/567 |
| 6,033,369 | A | 3/2000 | Goldenberg | 600/567 |
| 6,033,411 | A | 3/2000 | Preissman | 606/99 |
| 6,063,037 | A | 5/2000 | Mittermeier et al. | 600/567 |
| 6,071,284 | A | 6/2000 | Fox | 606/80 |
| 6,080,115 | A | 6/2000 | Rubinstein et al. | 600/567 |
| 6,083,176 | A | 7/2000 | Terwilliger | 600/562 |
| 6,086,543 | A | 7/2000 | Anderson et al. | 600/567 |
| 6,086,544 | A | 7/2000 | Hibner et al. | 600/568 |
| 6,096,042 | A | 8/2000 | Herbert | 606/80 |
| 6,102,915 | A | 8/2000 | Bresler et al. | 606/80 |
| 6,106,484 | A | 8/2000 | Terwilliger | 600/568 |
| 6,110,128 | A | 8/2000 | Andelin et al. | 600/566 |

(56) References Cited

U.S. PATENT DOCUMENTS

| | | | |
|---|---|---|---|
| 6,110,129 A | 8/2000 | Terwilliger | 600/567 |
| 6,110,174 A | 8/2000 | Nichter | 606/72 |
| 6,120,462 A | 9/2000 | Hibner et al. | 600/566 |
| 6,129,106 A | 10/2000 | Kornelson et al. | |
| 6,135,769 A | 10/2000 | Kwan | 433/80 |
| 6,159,163 A | 12/2000 | Strauss et al. | 600/566 |
| 6,162,203 A | 12/2000 | Haaga | 604/272 |
| 6,183,442 B1 | 2/2001 | Athanasiou et al. | 604/154 |
| 6,210,376 B1 | 4/2001 | Grayson | 604/264 |
| 6,217,561 B1 | 4/2001 | Gibbs | 604/264 |
| 6,221,029 B1 | 4/2001 | Mathis et al. | 600/564 |
| 6,228,049 B1 | 5/2001 | Schroeder et al. | 604/93.01 |
| 6,228,088 B1 | 5/2001 | Miller et al. | 606/80 |
| 6,231,996 B1 | 5/2001 | Umeno et al. | |
| 6,238,355 B1 | 5/2001 | Daum | 600/567 |
| 6,242,009 B1 | 6/2001 | Batarseh et al. | |
| 6,247,928 B1 * | 6/2001 | Meller et al. | 433/80 |
| 6,248,110 B1 | 6/2001 | Reiley et al. | 606/93 |
| 6,257,351 B1 | 7/2001 | Ark et al. | 173/178 |
| 6,272,007 B1 | 8/2001 | Kitlas et al. | |
| 6,273,715 B1 | 8/2001 | Meller et al. | 433/80 |
| 6,273,862 B1 | 8/2001 | Privitera et al. | 600/568 |
| 6,283,925 B1 | 9/2001 | Terwilliger | 600/568 |
| 6,283,970 B1 | 9/2001 | Lubinus | 606/80 |
| 6,287,114 B1 | 9/2001 | Meller et al. | 433/80 |
| 6,302,852 B1 | 10/2001 | Fleming et al. | 600/567 |
| 6,309,358 B1 | 10/2001 | Okubo | 600/466 |
| 6,312,394 B1 | 11/2001 | Fleming | 600/567 |
| 6,315,737 B1 | 11/2001 | Skinner | 600/566 |
| 6,325,806 B1 | 12/2001 | Fox | 606/80 |
| 6,328,701 B1 | 12/2001 | Terwilliger | 600/567 |
| 6,328,744 B1 | 12/2001 | Harari et al. | 606/80 |
| 6,358,252 B1 | 3/2002 | Shapira | 606/80 |
| 6,402,701 B1 | 6/2002 | Kaplan et al. | 600/567 |
| 6,419,490 B1 | 7/2002 | Kitchings Weathers, Jr. | 433/165 |
| 6,425,888 B1 | 7/2002 | Embleton et al. | 604/290 |
| 6,428,487 B1 | 8/2002 | Burdorff et al. | 600/568 |
| 6,443,910 B1 | 9/2002 | Krueger et al. | 600/567 |
| 6,458,117 B1 | 10/2002 | Pollins, Sr. | |
| 6,468,248 B1 | 10/2002 | Gibbs | 604/164.01 |
| 6,478,751 B1 | 11/2002 | Krueger et al. | 600/566 |
| 6,488,636 B2 | 12/2002 | Bryan et al. | 600/565 |
| 6,523,698 B1 | 2/2003 | Dennehey et al. | 210/435 |
| 6,527,736 B1 | 3/2003 | Attinger et al. | 604/43 |
| 6,527,778 B2 | 3/2003 | Athanasiou et al. | 606/80 |
| 6,540,694 B1 | 4/2003 | Van Bladel et al. | 600/564 |
| 6,547,511 B1 | 4/2003 | Adams | 414/46.4 |
| 6,547,561 B2 | 4/2003 | Meller et al. | 433/80 |
| 6,550,786 B2 | 4/2003 | Gifford et al. | |
| 6,554,779 B2 | 4/2003 | Viola et al. | 600/568 |
| 6,555,212 B2 | 4/2003 | Boiocchi et al. | 428/295.4 |
| 6,575,919 B1 * | 6/2003 | Reiley et al. | 600/567 |
| 6,585,622 B1 | 7/2003 | Shum et al. | 482/8 |
| 6,595,911 B2 | 7/2003 | LoVuolo | 600/30 |
| 6,595,979 B1 | 7/2003 | Epstein et al. | 604/506 |
| 6,613,054 B2 | 9/2003 | Scribner et al. | 606/93 |
| 6,616,632 B2 | 9/2003 | Sharp et al. | 604/117 |
| 6,620,111 B2 | 9/2003 | Stephens et al. | 600/567 |
| 6,626,848 B2 | 9/2003 | Neuenfeldt | 600/564 |
| 6,626,887 B1 | 9/2003 | Wu | 604/512 |
| 6,638,235 B2 | 10/2003 | Miller et al. | 600/566 |
| 6,656,133 B2 | 12/2003 | Voegele et al. | 600/568 |
| 6,689,072 B2 | 2/2004 | Kaplan et al. | 600/567 |
| 6,702,760 B2 | 3/2004 | Krause et al. | 600/564 |
| 6,702,761 B1 | 3/2004 | Damadian et al. | 600/576 |
| 6,706,016 B2 | 3/2004 | Cory et al. | 604/117 |
| 6,716,192 B1 | 4/2004 | Orosz, Jr. | 604/117 |
| 6,716,215 B1 | 4/2004 | David et al. | 606/80 |
| 6,716,216 B1 | 4/2004 | Boucher et al. | 606/86 |
| 6,730,043 B2 | 5/2004 | Krueger et al. | 600/567 |
| 6,730,044 B2 | 5/2004 | Stephens et al. | 600/568 |
| 6,749,576 B2 | 6/2004 | Bauer | 600/567 |
| 6,752,768 B2 | 6/2004 | Burdorff et al. | 600/568 |
| 6,752,816 B2 | 6/2004 | Culp et al. | 606/170 |
| 6,758,824 B1 | 7/2004 | Miller et al. | 600/568 |
| 6,761,726 B1 | 7/2004 | Findlay et al. | 606/182 |
| 6,796,957 B2 | 9/2004 | Carpenter et al. | 604/93.01 |
| 6,846,314 B2 | 1/2005 | Shapira | 606/80 |
| 6,849,051 B2 | 2/2005 | Sramek et al. | 600/565 |
| 6,855,148 B2 | 2/2005 | Foley et al. | 606/86 |
| 6,860,860 B2 | 3/2005 | Viola | 600/564 |
| 6,875,183 B2 | 4/2005 | Cervi | 600/567 |
| 6,884,245 B2 | 4/2005 | Spranza | 606/79 |
| 6,887,209 B2 | 5/2005 | Kadziauskas et al. | 600/565 |
| 6,890,308 B2 | 5/2005 | Islam | 600/564 |
| 6,905,486 B2 | 6/2005 | Gibbs | 604/510 |
| 6,930,461 B2 | 8/2005 | Rutkowski | 318/567 |
| 6,942,669 B2 | 9/2005 | Kurc | 606/80 |
| 6,969,373 B2 | 11/2005 | Schwartz et al. | 604/170.03 |
| 7,008,381 B2 | 3/2006 | Janssens | 600/564 |
| 7,008,383 B1 | 3/2006 | Damadian et al. | 600/567 |
| 7,008,394 B2 | 3/2006 | Geise et al. | 615/6.15 |
| 7,025,732 B2 | 4/2006 | Thompson et al. | 600/654 |
| 7,063,672 B2 | 6/2006 | Schramm | 600/564 |
| 7,081,123 B2 * | 7/2006 | Merboth et al. | 606/185 |
| 7,137,985 B2 | 11/2006 | Jahng | 606/61 |
| 7,186,257 B2 | 3/2007 | Kim | |
| 7,207,949 B2 | 4/2007 | Miles et al. | 600/554 |
| 7,212,011 B2 | 5/2007 | Shimizu et al. | |
| 7,226,450 B2 | 6/2007 | Athanasiou et al. | 606/80 |
| 7,229,401 B2 | 6/2007 | Kindlein | 600/7 |
| 7,670,328 B2 | 3/2010 | Miller | |
| 7,699,850 B2 | 4/2010 | Miller | |
| 7,811,260 B2 | 10/2010 | Miller et al. | |
| 7,815,642 B2 | 10/2010 | Miller | |
| 7,850,620 B2 | 12/2010 | Miller et al. | |
| 7,899,528 B2 | 3/2011 | Miller et al. | |
| 7,951,089 B2 | 5/2011 | Miller | |
| 8,038,664 B2 | 10/2011 | Miller et al. | |
| 8,142,365 B2 | 3/2012 | Miller | |
| 9,110,104 B2 | 8/2015 | Chung et al. | |
| 2001/0005778 A1 | 6/2001 | Ouchi | |
| 2001/0014439 A1 | 8/2001 | Meller et al. | 466/50 |
| 2001/0047183 A1 | 11/2001 | Privitera et al. | 606/170 |
| 2001/0053888 A1 | 12/2001 | Athanasiou et al. | 604/154 |
| 2002/0042581 A1 | 4/2002 | Cervi | 600/567 |
| 2002/0055713 A1 | 5/2002 | Gibbs | 604/164.01 |
| 2002/0120212 A1 | 8/2002 | Ritchart et al. | 600/567 |
| 2002/0138021 A1 | 9/2002 | Pflueger | 600/565 |
| 2003/0028146 A1 | 2/2003 | Aves | 604/164.06 |
| 2003/0032939 A1 | 2/2003 | Gibbs | 604/510 |
| 2003/0036747 A1 | 2/2003 | Ie et al. | 606/1 |
| 2003/0050574 A1 | 3/2003 | Krueger | 600/567 |
| 2003/0078586 A1 | 4/2003 | Shapira | |
| 2003/0114858 A1 | 6/2003 | Athanasiou et al. | 606/80 |
| 2003/0125639 A1 | 7/2003 | Fisher et al. | 600/564 |
| 2003/0153842 A1 | 8/2003 | Lamoureux et al. | 600/564 |
| 2003/0191414 A1 | 10/2003 | Reiley et al. | 600/567 |
| 2003/0195436 A1 | 10/2003 | Van Bladel et al. | 600/584 |
| 2003/0195524 A1 | 10/2003 | Barner | 606/119 |
| 2003/0199787 A1 | 10/2003 | Schwindt | 600/568 |
| 2003/0216667 A1 | 11/2003 | Viola | 600/564 |
| 2003/0225344 A1 | 12/2003 | Miller | 600/568 |
| 2003/0225364 A1 | 12/2003 | Kraft et al. | 604/35 |
| 2003/0225411 A1 | 12/2003 | Miller | |
| 2004/0010236 A1 * | 1/2004 | Morawski et al. | 604/272 |
| 2004/0019297 A1 | 1/2004 | Angel | 600/564 |
| 2004/0019299 A1 | 1/2004 | Ritchart et al. | 600/567 |
| 2004/0034280 A1 | 2/2004 | Privitera et al. | 600/170 |
| 2004/0049128 A1 | 3/2004 | Miller et al. | 600/566 |
| 2004/0064136 A1 | 4/2004 | Papineau et al. | 606/41 |
| 2004/0073139 A1 | 4/2004 | Hirsch et al. | |
| 2004/0092946 A1 | 5/2004 | Bagga et al. | 606/93 |
| 2004/0127814 A1 * | 7/2004 | Negroni | A61B 10/025 600/567 |
| 2004/0153003 A1 | 8/2004 | Cicenas et al. | 600/564 |
| 2004/0158172 A1 | 8/2004 | Hancock | 600/564 |
| 2004/0158173 A1 | 8/2004 | Voegele et al. | 600/568 |
| 2004/0162505 A1 | 8/2004 | Kaplan et al. | 600/567 |
| 2004/0191897 A1 | 9/2004 | Muschler | 435/325 |
| 2004/0210161 A1 | 10/2004 | Burdorff et al. | 600/566 |
| 2004/0215102 A1 | 10/2004 | Ikehara et al. | |
| 2004/0220497 A1 | 11/2004 | Findlay et al. | 600/562 |

(56) References Cited

U.S. PATENT DOCUMENTS

| | | |
|---|---|---|
| 2005/0027210 A1 | 2/2005 | Miller .......................... 600/567 |
| 2005/0040060 A1 | 2/2005 | Andersen et al. ........... 206/363 |
| 2005/0075581 A1 | 4/2005 | Schwindt ..................... 600/568 |
| 2005/0085838 A1 | 4/2005 | Thompson et al. .......... 606/170 |
| 2005/0101880 A1 | 5/2005 | Cicenas et al. .............. 600/567 |
| 2005/0113716 A1 | 5/2005 | Mueller, Jr. et al. ......... 600/568 |
| 2005/0124915 A1 | 6/2005 | Eggers et al. ................ 600/568 |
| 2005/0131345 A1 | 6/2005 | Miller .......................... 604/117 |
| 2005/0148940 A1 | 7/2005 | Miller .......................... 604/187 |
| 2005/0165328 A1 | 7/2005 | Heske et al. ................. 600/566 |
| 2005/0165403 A1 | 7/2005 | Miller ............................ 606/79 |
| 2005/0165404 A1 | 7/2005 | Miller ............................ 606/80 |
| 2005/0171504 A1 | 8/2005 | Miller .......................... 604/506 |
| 2005/0182394 A1 | 8/2005 | Spero et al. ................... 606/21 |
| 2005/0200087 A1 | 9/2005 | Vasudeva et al. ............ 279/143 |
| 2005/0203439 A1 | 9/2005 | Heske et al. ................. 600/566 |
| 2005/0209530 A1 | 9/2005 | Pflueger ....................... 600/567 |
| 2005/0215921 A1 | 9/2005 | Hibner et al. ................ 600/566 |
| 2005/0228309 A1 | 10/2005 | Fisher et al. ................. 600/562 |
| 2005/0261693 A1 | 11/2005 | Miller et al. ................... 606/80 |
| 2006/0011506 A1 | 1/2006 | Riley ........................... 206/570 |
| 2006/0015066 A1 | 1/2006 | Turieo et al. ................. 604/136 |
| 2006/0036212 A1 | 2/2006 | Miller ............................ 604/48 |
| 2006/0052790 A1 | 3/2006 | Miller ............................ 606/80 |
| 2006/0074345 A1 | 4/2006 | Hibner ......................... 600/566 |
| 2006/0079774 A1 | 4/2006 | Anderson ..................... 600/442 |
| 2006/0089565 A1 | 4/2006 | Schramm ..................... 600/566 |
| 2006/0122535 A1 | 6/2006 | Daum .......................... 600/565 |
| 2006/0129082 A1 | 6/2006 | Rozga .......................... 604/6.04 |
| 2006/0144548 A1 | 7/2006 | Beckman et al. ................ 163/1 |
| 2006/0149163 A1 | 7/2006 | Hibner et al. ................ 600/566 |
| 2006/0167377 A1 | 7/2006 | Ritchart et al. .............. 600/566 |
| 2006/0167378 A1 | 7/2006 | Miller .......................... 600/566 |
| 2006/0167379 A1 | 7/2006 | Miller .......................... 600/566 |
| 2006/0184063 A1 | 8/2006 | Miller .......................... 600/568 |
| 2006/0189940 A1 | 8/2006 | Kirsch ......................... 604/164.1 |
| 2007/0016100 A1 | 1/2007 | Miller .......................... 600/567 |
| 2007/0049945 A1 | 3/2007 | Miller ............................ 606/86 |
| 2007/0149920 A1 | 6/2007 | Michels et al. ............. 604/93.01 |
| 2007/0213735 A1 | 9/2007 | Saadat et al. .................... 606/79 |
| 2007/0270775 A1 | 11/2007 | Miller et al. ................. 604/506 |
| 2008/0015467 A1 | 1/2008 | Miller .......................... 600/568 |
| 2008/0015468 A1 | 1/2008 | Miller .......................... 600/568 |
| 2008/0045857 A1 | 2/2008 | Miller .......................... 600/566 |
| 2008/0045860 A1 | 2/2008 | Miller et al. ................. 600/567 |
| 2008/0045861 A1 | 2/2008 | Miller et al. ................. 600/567 |
| 2008/0045965 A1 | 2/2008 | Miller et al. ................... 606/80 |
| 2008/0140014 A1 | 6/2008 | Miller et al. ................. 604/180 |
| 2008/0215056 A1 | 9/2008 | Miller et al. ................... 606/80 |
| 2008/0221580 A1 | 9/2008 | Miller et al. ................... 606/80 |

FOREIGN PATENT DOCUMENTS

| | | | |
|---|---|---|---|
| CN | 2320209 Y | 5/1999 | ............ A61B 17/34 |
| DE | 10057931 A1 | 11/2000 | ............ A61B 17/32 |
| DE | 10057831 A1 | 5/2002 | |
| EP | 517000 | 12/1992 | ............ A61M 5/168 |
| EP | 0807412 A1 | 11/1997 | ............ A61B 17/32 |
| EP | 1099450 | 5/2001 | ............ A61M 5/32 |
| EP | 1314452 | 5/2003 | |
| EP | 2177171 B1 | 8/2012 | |
| FR | 853349 | 3/1940 | |
| FR | 2457105 | 5/1979 | ............ A61M 5/00 |
| FR | 2516386 | 11/1981 | ............ A61M 5/18 |
| GB | 2130890 | 6/1984 | ............ A61B 10/00 |
| JP | 1052433 | 2/1989 | ............ A61B 1/00 |
| JP | 2001505076 A | 4/2001 | |
| WO | 9307819 | 4/1993 | ............ A61B 17/32 |
| WO | 9631164 | 10/1996 | ............ A61B 17/34 |
| WO | 9806337 | 2/1998 | ............ A61B 17/16 |
| WO | 99/18866 | 4/1999 | ............ A61B 17/34 |
| WO | 9952444 | 10/1999 | ............ A61B 17/00 |
| WO | 00/56220 | 9/2000 | ............ A61B 10/00 |
| WO | 01/78590 | 10/2001 | ............ A61B 5/00 |
| WO | 0241792 | 5/2002 | ............ A61B 17/16 |
| WO | 02096497 | 12/2002 | ............ A61M 31/00 |
| WO | 2005110259 | 11/2005 | ............ A61B 17/88 |
| WO | 2005112800 | 12/2005 | ............ A61B 17/34 |
| WO | 2008081438 | 7/2008 | |

OTHER PUBLICATIONS

International Preliminary Report on Patentability, PCT/US2007/072217, 11 pages, Mailed Feb. 12, 2009.
Official Action for European Application No. 03756317.8 (4 pages), Dec. 28, 2006.
Invitation to Pay Additional Fees for Application No. PCT/US2006/025201 (6 pages), Oct. 26, 2006.
Australian Exam Report on Patent Application No. 2003240970, 2 pages, Oct. 15, 2007.
International Search Report and Written Opinion for International Application No. PCT/US2006/025201 (18 pages), Jan. 29, 2007.
International Search Report, PCT/US2007/072209, 9 pages, Mailing Date Mar. 12, 2007.
International Search Report, PCT/US2007/072217, 9 pages, Mailing Date Mar. 12, 2007.
Preliminary Report on Patentability, PCT/US2006/025201, 12 pages, Mailing Date Feb. 7, 2008.
Gunal et al., Compartment Syndrome After Intraosseous Infusion: An Expiremental Study in Dogs, Journal od Pediatric Surgery, vol. 31, No. 11, pp. 1491-1493, Nov. 1996.
International Search Report, PCT/US2007/072217, 20 pages, Mailing Date Mar. 31, 2008.
International Search Report, PCT/US2007/072209, 18 pages, Mailing Date Apr. 25, 2008.
Communication Pursuant to Article 94(3) EPC, Application No. 05 712 091.7-1265, 4 pages, Apr. 8, 2008.
Notification of the Chinese Office Action, Application No. 200580003261.81, 3 pages, Mar. 1, 2008.
International Search Report and Written Opinion, PCT/US08/500346, 12 pages, Mailing Date May 22, 2008.
Chinese Office Action, Application No. 2005800003261, (with English translation), (9 pgs), Jan. 16, 2009.
Japanese Office Action, Application No. 2004-508,670, (with English summary), (13 pgs), Jan. 16, 2009.
PCT Preliminary Report on Patentability, PCT/US/2008/050346, (8 pgs), Jul. 23, 2009.
European Office Action and Search Report, Application No. 09150973.7, 8 pages, Oct. 23, 2009.
International Preliminary Report on Patentability, PCT/US08/52943, 7 pages, Mailed Oct. 15, 2009.
Japanese Office Action, Application No. 2004-508,669, (with English summary), (9 pgs), Aug. 3, 2009.
Chinese Office Action, Application No. 200780000590.6, (with English translation), (13 pgs), Aug. 21, 2009.
International Preliminary Report on Patentability PCT/US2005/002484, 9 pages, Mailed Aug. 3, 2006.
International PCT Search Report and Written Opinion PCT/US2004/037753, 16 pages, Mailed Jul. 8, 2005.
International PCT Search Report and Written Opinion PCT/US2005/002484, 15 pages, Mailed, Jul. 22, 2005.
International Preliminary Report on Patentability, PCT/US/2007/078203, 13 pages, Mar. 26, 2009.
International Preliminary Report on Patentability, PCT/US/2007/078207, 10 pages, Mar. 26, 2009.
International Preliminary Report on Patentability, PCT/US/2007/078205, 10 pages, Mar. 26, 2009.
International Preliminary Report on Patentability, PCT/US/2007/078204, 11 pages, Apr. 2, 2009.
Vidacare Corporation Comments to Intraosseous Vascular Access Position Paper, Infusion Nurses Society, 6 pages, May 4, 2009.
International Preliminary Report on Patentability, PCT/US/2007/072209, 10 pages, May 14, 2009.
Communication relating to the results of the partial International Search Report for PCT/US2005/002484, 6 pages, Mailed May 19, 2005.

(56) References Cited

OTHER PUBLICATIONS

Richard O. Cummings et al., "ACLS-Principles and Practice", ACLS—The Reference Textbook, American Heart Association, pp. 214-218, 2003.
International PCT Search Report, PCT/US03/17167, 8 pages, Mailed Sep. 16, 2003.
International PCT Search Report, PCT/US03/17203, 8 pages, Mailed Sep. 16, 2003.
International PCT Search Report PCT/US2004/037753, 6 pages, Mailed Apr. 19, 2005.
Äström, K.G., "Automatic Biopsy Instruments Used Through a Coaxial Bone Biopsy System with an Eccentric Drill Tip," Acta Radiologica, 1995; 36:237-242, May 1995.
Äström, K. Gunnar O., "CT-guided Transsternal Core Biopsy of Anterior Mediastinal Masses," Radiology 1996; 199:564-567, May 1996.
International PCT Search Report PCT/US03/17167, 8 pages, Mailed Sep. 16, 2003.
International PCT Search Report PCT/US03/17203, 8 pages, Mailed Sep. 16, 2003.
International PCT Search Report and Written Opinion PCT/US2005/002484, 15 pages, Mailed Jul. 22, 2005.
Cummins, Richard O., et al, "ACLS-Principles and Practice", ACLS—The Reference Textbook, American Heart Association, pp. 214-218, 2003.
Riley et al., "A Pathologist's Perspective on Bone Marrow Aspiration Biopsy: I. Performing a Bone Marrow Examination," Journal of Clinical Laboratory Analysis 18, pp. 70-90, 2004.
Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org, Feb. 21, 2007.
Liakat A. Parapia, Trepanning or trephines: a history of bone marrow biopsy, British Journal of Haematology, pp. 14-19 2007.
Pediatric Emergency, Intraosseous Infusion for Administration of Fluids and Drugs, www.cookgroup.com, 1 pg, 2000.
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages, 2008.
Buckley et al., CT-guided bone biopsy: Initial experience with commercially available hand held Black and Decker drill, European Journal of Radiology 61, pp. 176-180, 2007.
Hakan et al., CT-guided Bone BiopsyPerformed by Means of Coaxial Bopsy System with an Eccentric Drill, Radiology, pp. 549-552, Aug. 1993.
European Search Report 08158699.2-1265, 4 pages, Aug. 2008.
International Search Report and Written Opinion, PCT/US2007/078204, 14 pages, May 15, 2008.
International Search Report and Written Opinion, PCT/US08/52943, 8 pages, Sep. 26, 2008.
European Office Action Communication, Application No. 08158699.2-1265/1967142, 10 pages, Mailing Date Nov. 4, 2008.
PCT Invitation to Pay Additional Fees, PCT/US2007/072209, 9 pages, Mailing Dec. 3, 2007.
"Proven reliability for quality bone marrow samples", Special Procedures, Cardinal Health, 6 pages, 2003.
F.A.S.T. 1 Intraosseous Infusion System with Depth-Control Mechanism Brochure, 6 pages, 2000.
BioAccess.com, Single Use Small Bone Power Tool—How It Works, 1 pg, Printed Jun. 9, 2008.
International Search Report and Written Opinion, PCT/US2007/078203, 15 pages, Mailing Date May 13, 2008.
International Search Report and Written Opinion, PCT/US2007/072202, 17 pages, Mailing Date Mar. 25, 2008.
International Search Report and Written Opinion, PCT/US2007/078207, 13 pages, Mailing Date Apr. 7, 2008.
International Search Report and Written Opinion, PCT/US2007/078205, 13 pages, Mailing date Sep. 11, 2007.
European Office Action EP03731475.4, 4 pages, Oct. 11, 2007.
Liakat A. Parapia, Trepanning or trephines: a history of bone marrow biopsy, British Journal of Haematology, pp. 14-19, 2007.
Chinese Office Action with English translation; Application No. 200910006631.3; pp. 12, Mar. 11, 2010.
European Extended Search Report, Application No. EP10153350.3, 5 pages, Mar. 11, 2010.
Chinese Office Action with English translation; Application No. 200910006631.3; pp. 13, Mar. 11, 2010.
Taiwan Office Action, Application No. 94102179 (with English translation); 12 pages, May 13, 2010.
Japanese Office Action, Application No. 2004-508,670, (with English summary), (13 pgs), Apr. 21, 2009.
European Office Action and Search Report, Application No. 09150973.7, (8 pgs), Oct. 23, 2009.
Chinese Office Action with English translation; Application No. 200910006631.3; pp. 9, Nov. 11, 2010.
Chinese Office Action, Application No. 2009100066313; 12 pgs (Mar. 11, 2010).
Chinese Office Action, Application No. 2009100066313; 9 pgs (Nov. 11, 2010).
European Extended Search Report for European application 08021732.6 (Nov. 13, 2009).
European Office Action sent Jan. 19, 2011 and Response sent Jul. 21, 2011, EP Application No. 09150973.7.
European Office Action sent Dec. 22, 2011 and Response sent Jun. 29, 2012, EP Application No. 09150973.7.
European Office Action sent Feb. 21, 2007 and Response sent Jun. 27, 2007, EP Application No. 05712091.7.
European Office Action sent Apr. 8, 2008 and Response sent May 15, 2008, EP Application No. 05712091.7.
European Office Action sent Sep. 21, 2007 and Response sent Nov. 26, 2007, EP Application No. 05712091.7.
European Office Action sent Sep. 8, 2010 and Response sent Mar. 17, 2011, EP Application No. 10123350.3.
European Office Action, Application No. 10 153 350.3, 5 pgs (Sep. 8, 2010).
Office Action for European application 03731475.4 (Oct. 11, 2007).
Office Action for European application 09155111.9-2310 (Nov. 25, 2009).
Office Action for Chinese application 200680021872.X (Nov. 6, 2009).
Taiwan Office Action, Application No. 94102179; 8 pgs (May 13, 2010).
Office Action for Chinese application 200780001198.3 (Apr. 27, 2010).
Office Action for Chinese application 200880000182.5 (Sep. 10, 2010).
Office Action issued in Chinese Application No. 200910006631.3, dated Mar. 22, 2011.
European Patent Office Communication for European Patent Appl. No. 09150973.7-1269 (mailed Dec. 22, 2011).
European Patent Office Communication for European Patent Appl. No. 10153350.3-1269 (mailed Sep. 8, 2010).
European Patent Office Communication for European Patent Appl. No. 09150973.7-1269 (mailed Jan. 19, 2011).

* cited by examiner

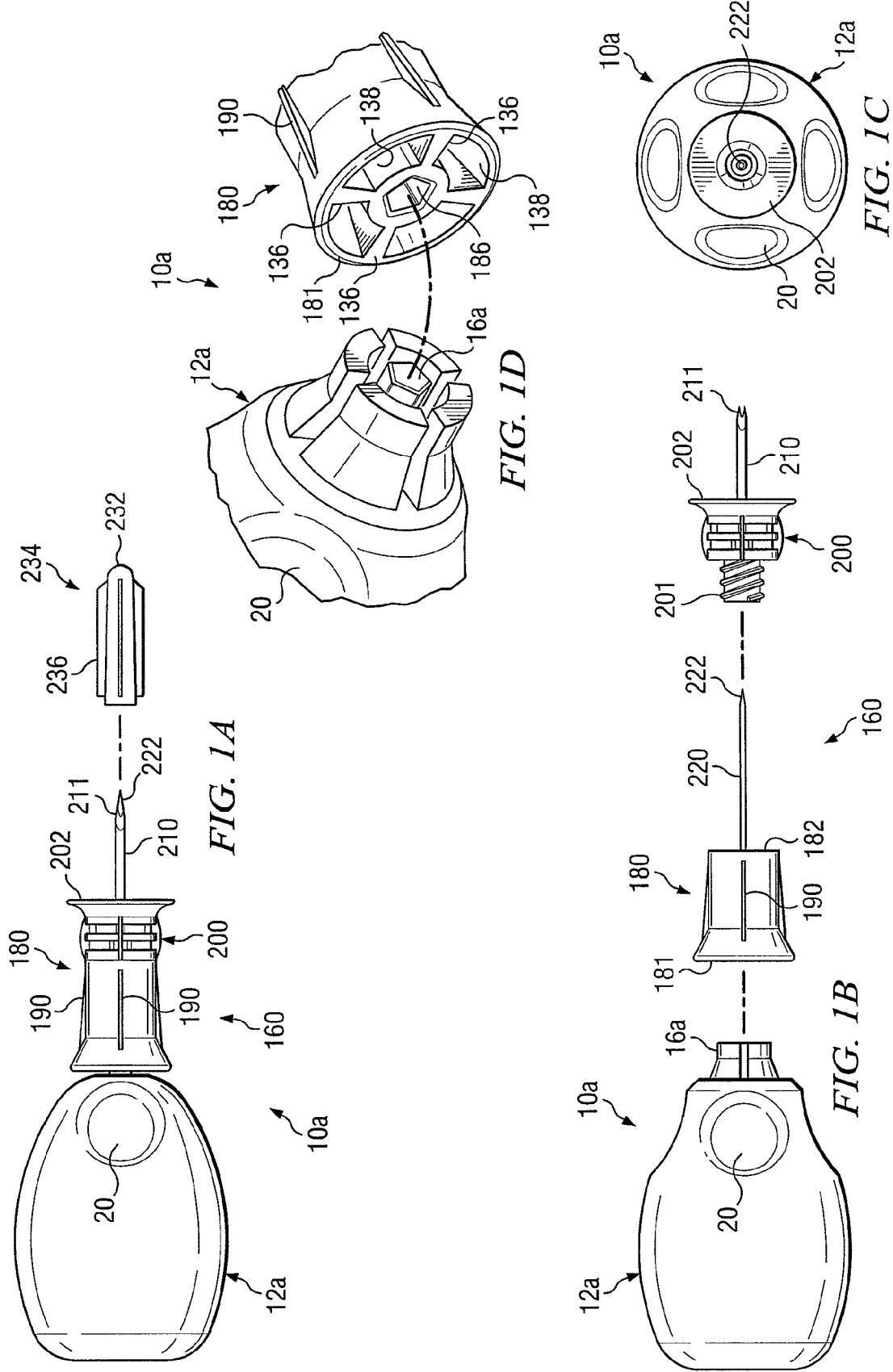

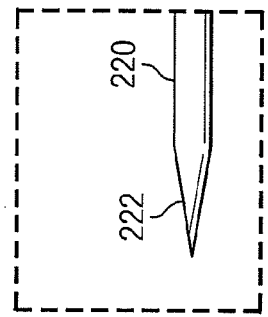
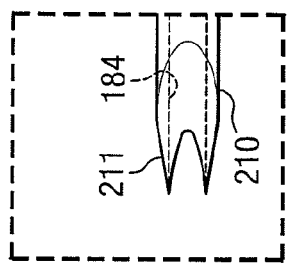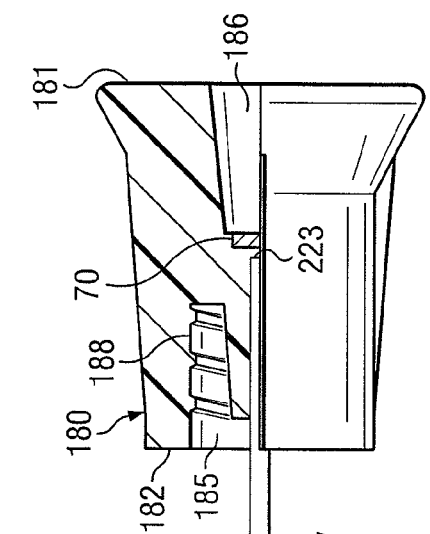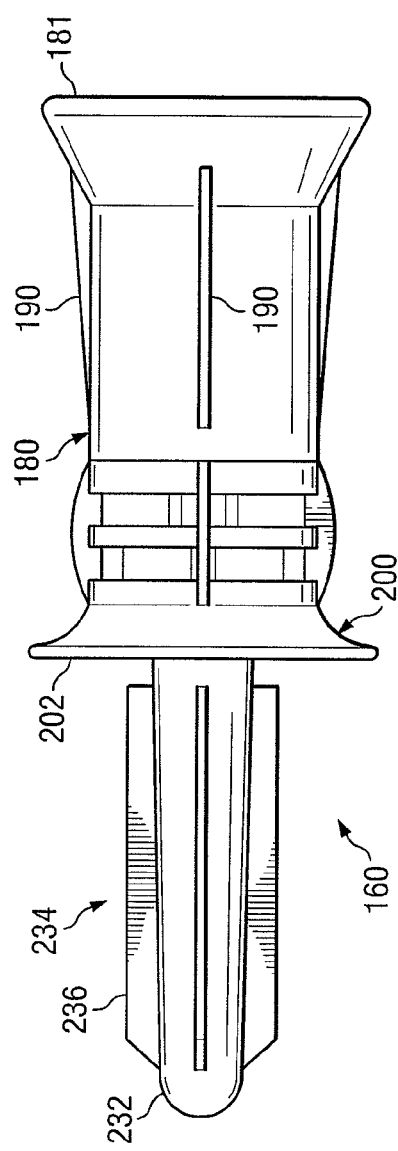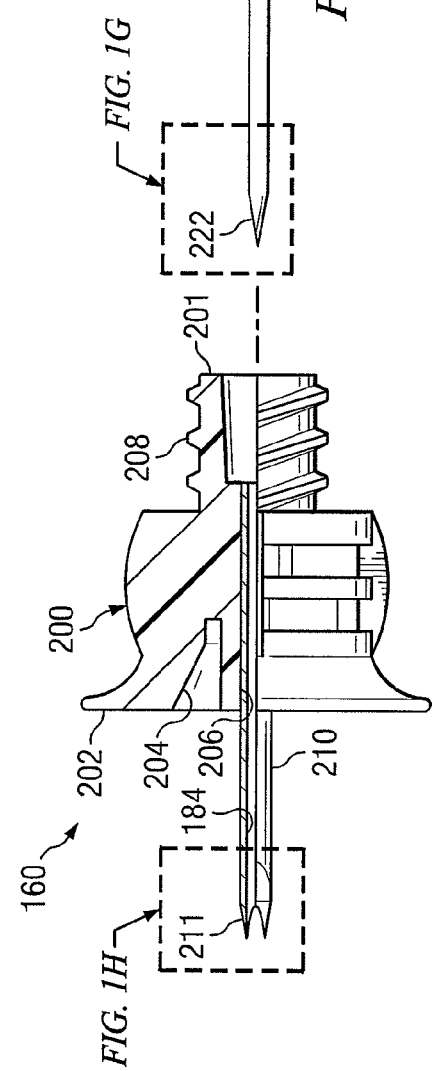

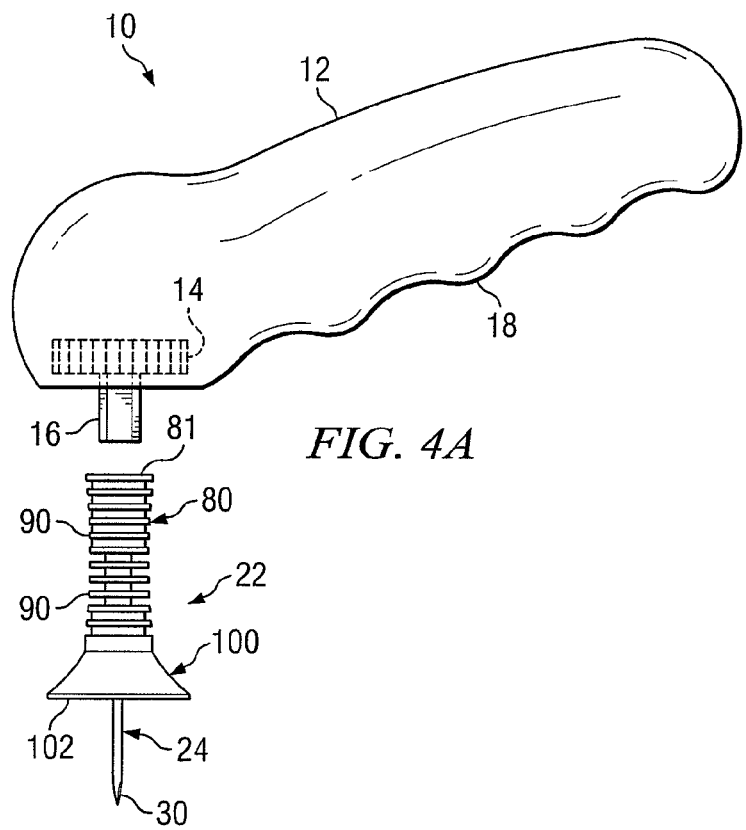
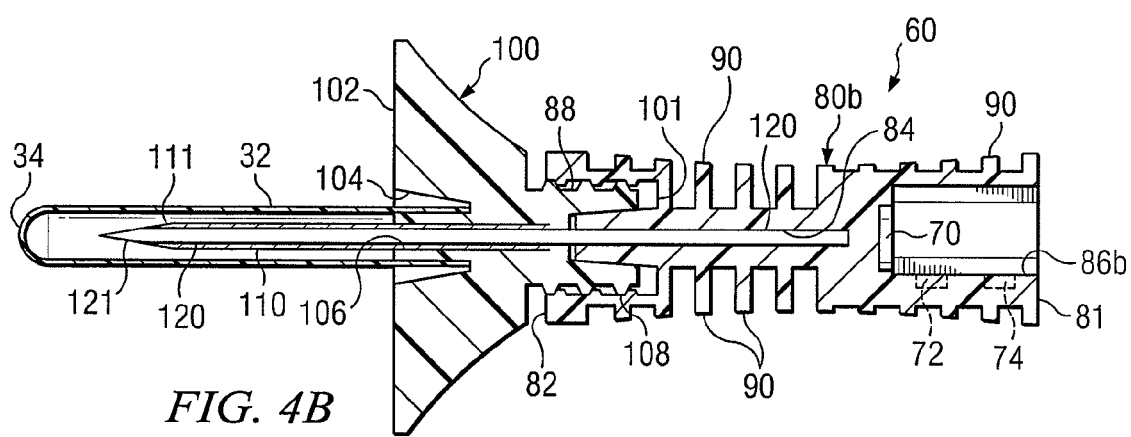

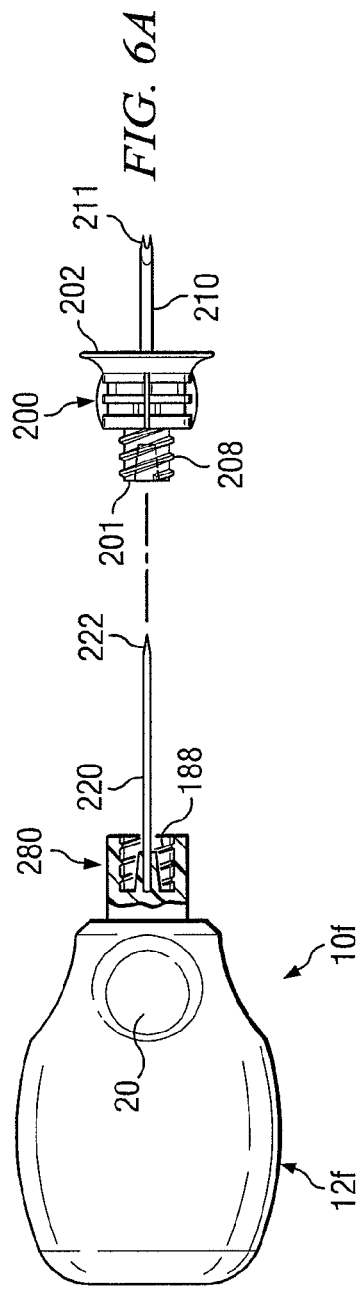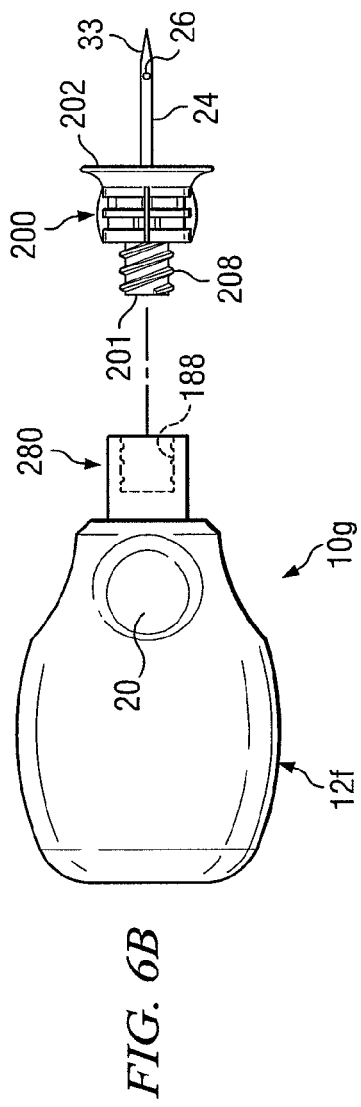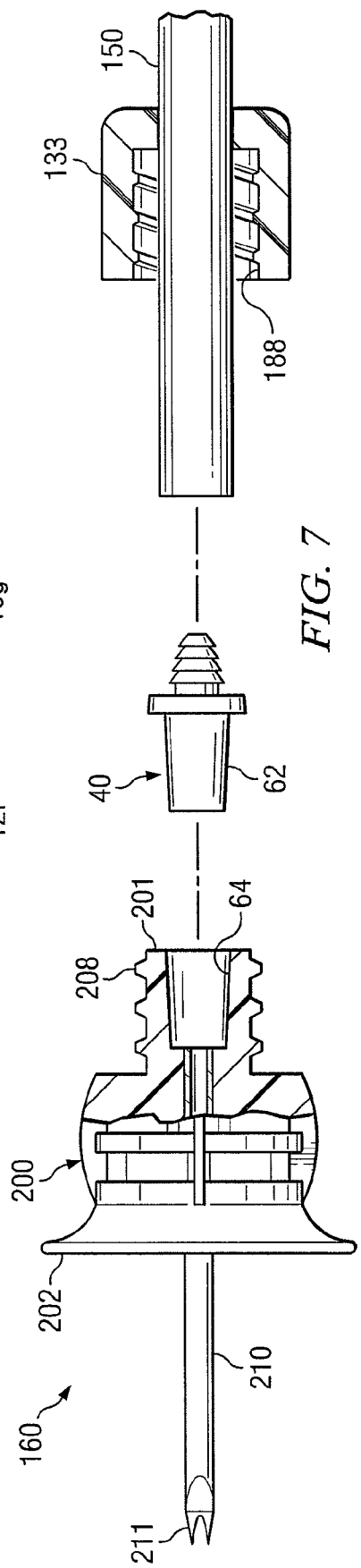
FIG. 6A
FIG. 6B
FIG. 7

US 9,433,400 B2

MANUAL INTRAOSSEOUS DEVICE

RELATED APPLICATION

This application is a divisional of U.S. patent application Ser. No. 11/042,912 filed Jan. 25, 2005 now U.S. Pat No. 8,641,715, which claims the benefit of Provisional Patent Application Ser. No. 60/539,171 entitled "Manual Interosseous Device" filed Jan. 26, 2004 and Provisional Patent Application Ser. No. 60/547,868 entitled "Impact-Driven Interosseous Needle" filed Feb. 26, 2004.

TECHNICAL FIELD

The present invention is related in general to a medical device to access bone marrow and more specifically to an apparatus and method for penetrating a bone and inserting a penetrator or needle into associated bone marrow.

BACKGROUND OF THE INVENTION

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

An essential element for treating all such emergencies is the rapid establishment of an intravenous (IV) line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. These patients are probed repeatedly with sharp needles in an attempt to solve this problem and may require an invasive procedure to finally establish an intravenous route.

A further complicating factor in achieving IV access occurs "in the field" e.g. at the scene of an accident or during ambulance transport where it is difficult to see the target and excessive motion make accessing the venous system very difficult.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

Many medical devices such as syringes, hypodermic needles, catheters, IV tubing and stop cocks may include either a pin (male) or box (female) Luer type fitting. The pin end or box end may include threads which allow releasably engaging an associated medical device with other equipment having a complimentary Luer type fitting. Luer type connections may sometimes be described as Luer slips or Luer locks. Luer slips may require a half twist of an associated collar to securely engage a pin end and a box end with each other. A Luer lock functions by forming a watertight fit between a pin and a box when engaged and when twisted by a half turn or more. Luer locks frequently include a threaded locking collar on a box end which mates with ears or projections from an associated pin end to provide a more positive, locked connection. Luer connections generally form fluid tight seals. Some Luer connections may include tapered fittings.

SUMMARY OF THE INVENTION

In accordance with teachings of the present invention, an apparatus and method for communicating with or accessing bone marrow of a bone are provided. The apparatus may include a handle having a drive shaft, a connector having a first end operable to connect to the drive shaft and a second end operable to attach to a penetrator hub. The penetrator hub may include a penetrator operable to access the bone marrow.

In an alternate embodiment an apparatus for manually penetrating a bone and associated bone marrow is provided. The apparatus may include a handle having at least one drive shaft, a releasable connector with a first end operable to attach to the at least one drive shaft and a second end operable to attach to a penetrator hub. The penetrator hub having a fitting operable to attach to the connector and a penetrator operable to access the bone marrow.

In another embodiment a method of accessing bone marrow of a bone is provided. The method may include inserting a penetrator into the bone marrow using an apparatus having a handle, a drive shaft and a connector with a first end operable to connect to the drive shaft and a second end operable to connect to a penetrator assembly. For some applications, a trocar may be disposed within the penetrator assembly. After inserting portions the penetrator assembly into the bone marrow, the handle and connector may be detached from the penetrator assembly. The trocar, when used, may be removed from the penetrator assembly and associated penetrator.

In various embodiments of the apparatus the handle may be T-shaped, pistol-shaped, round or oval-shaped, an ergonomically designed grip or any other shape suitable for general or specific use. In various embodiments the handle may include a compartment for enclosing an interosseous needle, a penetrator and associated trocar or any other accessory suitable for use with the apparatus.

In another embodiment a power driven apparatus for penetrating bone marrow of a bone may be provided. The apparatus may include a housing, a motor, a gear assembly, at least one drive shaft and a power source, and at least one drive shaft operable to connect to an auxiliary device and further operable to provide rotational energy to the auxiliary device. In various embodiments the auxiliary devices may include a ring cutter, a suction machine, or a flashlight.

Apparatus and methods incorporating teachings of the present invention may be used to access the bone marrow of any bone in a human or animal's body for any purpose including the delivery of fluids, medications, drugs, chemicals and any other bioactive substances including blood. Teachings of the present invention may also be used for harvesting bone marrow and/or stem cell. Teachings of the present invention may also be used to access body tissue or body cavities other than bone marrow in a human or animal species.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 1A shows an example illustration of an apparatus operable for penetrating bone marrow of a bone;

FIG. 1B is a schematic drawing showing an exploded view of the apparatus in FIG. 1A;

FIG. 1C is a schematic drawing showing an end view of the apparatus in FIG. 1A;

FIG. 1D is a schematic drawing showing one example of driver and connector incorporating teachings of the present invention;

FIG. 1E is a schematic drawing showing an example of a penetrator assembly which may be releasably engaged with a handle in accordance with teachings of the present invention;

FIG. 1F is a schematic drawing in section with portions broken away showing an exploded view of a penetrator assembly having an outer penetrator and an inner penetrator which may be releasably engaged with a handle in accordance with teachings of the present invention;

FIG. 1G is a schematic drawing showing an enlarged view of a tip formed on an inner penetrator which may be in accordance with teachings of the present invention;

FIG. 1H is a schematic drawing showing an enlarged view of a tip formed on an outer penetrator in accordance with teachings of the present invention;

FIG. 4A shows another example illustration of an apparatus for penetrating bone marrow of a bone in accordance with teachings of the present invention;

FIG. 4B is a schematic drawing in section with portions broken away showing one example of a penetrator assembly which may be releasably engaged with a drive shaft in accordance with teachings of the present invention;

FIG. 6A is a schematic drawing showing an exploded view of another example of apparatus operable for penetrating bone marrow of a bone in accordance with the teachings of the present invention;

FIG. 6B is a schematic drawing showing still another example of an apparatus operable for penetrating bone marrow of a bone in accordance with teachings of the present invention; and FIG. 7 is a schematic, exploded drawing showing one example of fitting satisfactory for attachment of tubing with a hub and penetrator in accordance with teachings of the present invention.

DETAILED DESCRIPTION OF THE INVENTION

Figure 1I:
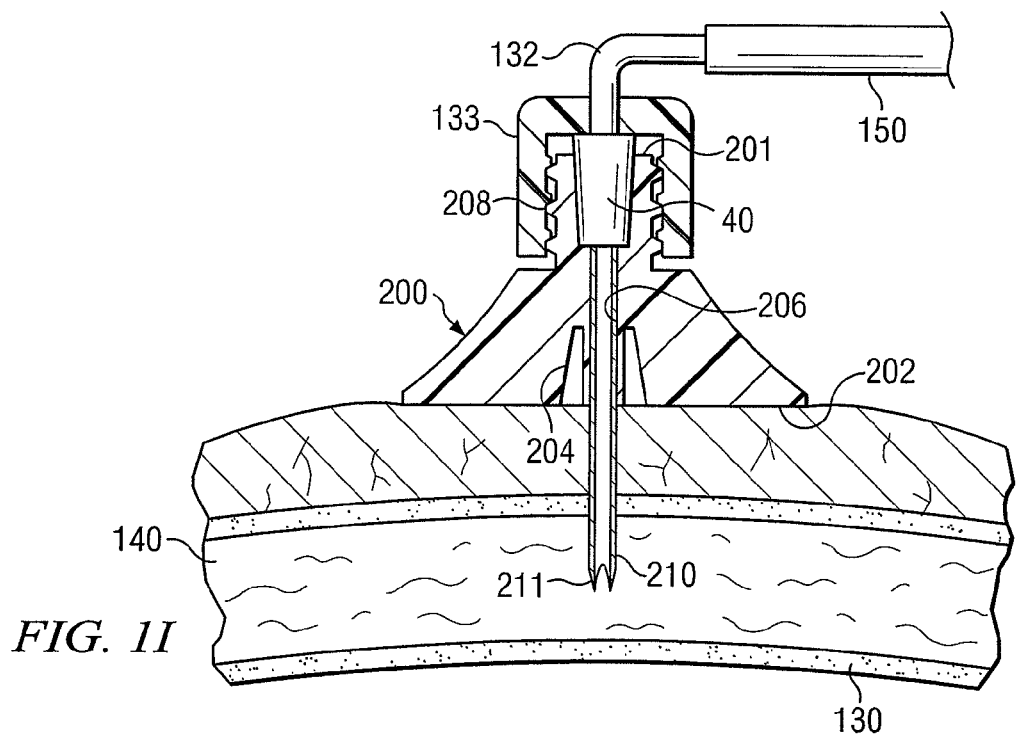
FIG. 1I is a schematic drawing in section and in elevation with portions broken away showing one example of an apparatus communicating with bone marrow of a bone in accordance with teachings of the present invention.

Some preferred embodiments of the invention and its advantages are best understood by reference to FIGS. 1A-7 wherein like numbers refer to same and like parts.

Various aspects of the present invention may be described with respect to treating human patients. However, apparatus and methods incorporating teachings of the present invention may be used to treat veterinary patients as well.

There are times when availability or advisability of having a battery powered driver for interosseous (IO) access is not possible. Such conditions may involve military special operations where extreme temperatures and severe weight restrictions limit what can be carried into battle. The same may be true for civilian emergency medical services (EMS) or first responders where long shelf life and infrequent use make the convenience of a battery powered driver impractical. For this reason, a manual driver offers certain advantages over a battery powered driver. Establishing interosseous access with a manual driver may sometimes take longer than with a powered driver. However, a bone may be penetrated and associated bone marrow accessed using either driver. When a manual driver is used, manual force may be exerted on a handle or grip to insert a penetrator or needle into the bone to access the bone marrow. A manual driver may also serve as a useful backup in cases where a battery powered driver fails to function, for example, due to a depleted power supply.

FIGS. 1A, 1B and 1C show one embodiment of manual driver 10a wherein handle 12a includes drive shaft 16a. Manual driver 10a may also include an optional ratchet mechanism such as shown in FIG. 3A. Handle 12a may be formed in a variety of shapes, such as with fingergrips 20. Handle 12a may be formed from materials satisfactory for multiple uses or may be formed from materials satisfactory for one time or disposable use. T-shaped handle 12e (See FIG. 3C), substantially round or oval shaped handle 12a (See FIGS. 1A and 1B), pistol-grip handle 12b (See FIG. 2) or any other ergonomically designed shape suitable for grasping with the hand or fingers during manual insertion of a penetrator may be used.

Various techniques may be satisfactorily used to releasably engage or attach a handle with an associated connector and/or penetrator in accordance with teachings of the present invention. For some applications a handle and an associated connector may be formed as a single unit. See FIGS. 6A and 6B. In such a configuration the handle/connector combination is operable to attach to a hub of a tissue penetrator. The handle and connector may or may not be detachable from each other. For other applications, a handle may be releasably engaged to a hub and associated penetrator without the use of a connector.

FIG. 1B shows apparatus 10a with the components separated. Handle 12a includes optional finger grips or finger rests 20. Drive shaft or attachment 16a may be releasably engaged with end 181 of connector 180. Inner penetrator or trocar 220 extends from end 182 of connector 180. Connector 180 and attached inner penetrator 220 may be releasably engaged with each other by Luer type fittings, threaded connections or other suitable fittings formed on first end 201 of hub 200. Outer penetrator 210 extends from second end 202 of hub 200.

FIG. 1C shows an end on view of apparatus 10a.

Figure 5A:
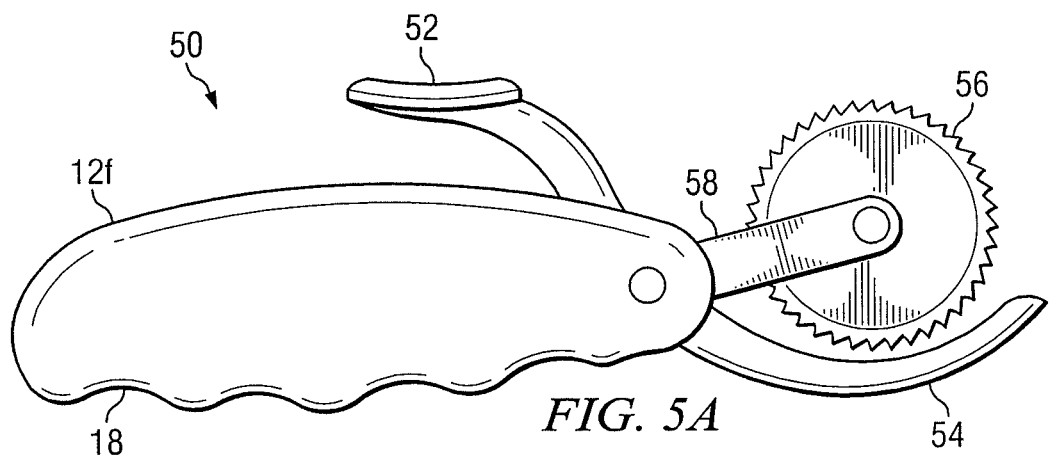
FIG. 5A shows an example illustration of an auxiliary device which may be modified for use with apparatus operable for penetrating bone marrow of a bone in accordance with teachings of the present invention.
Figure 5B:
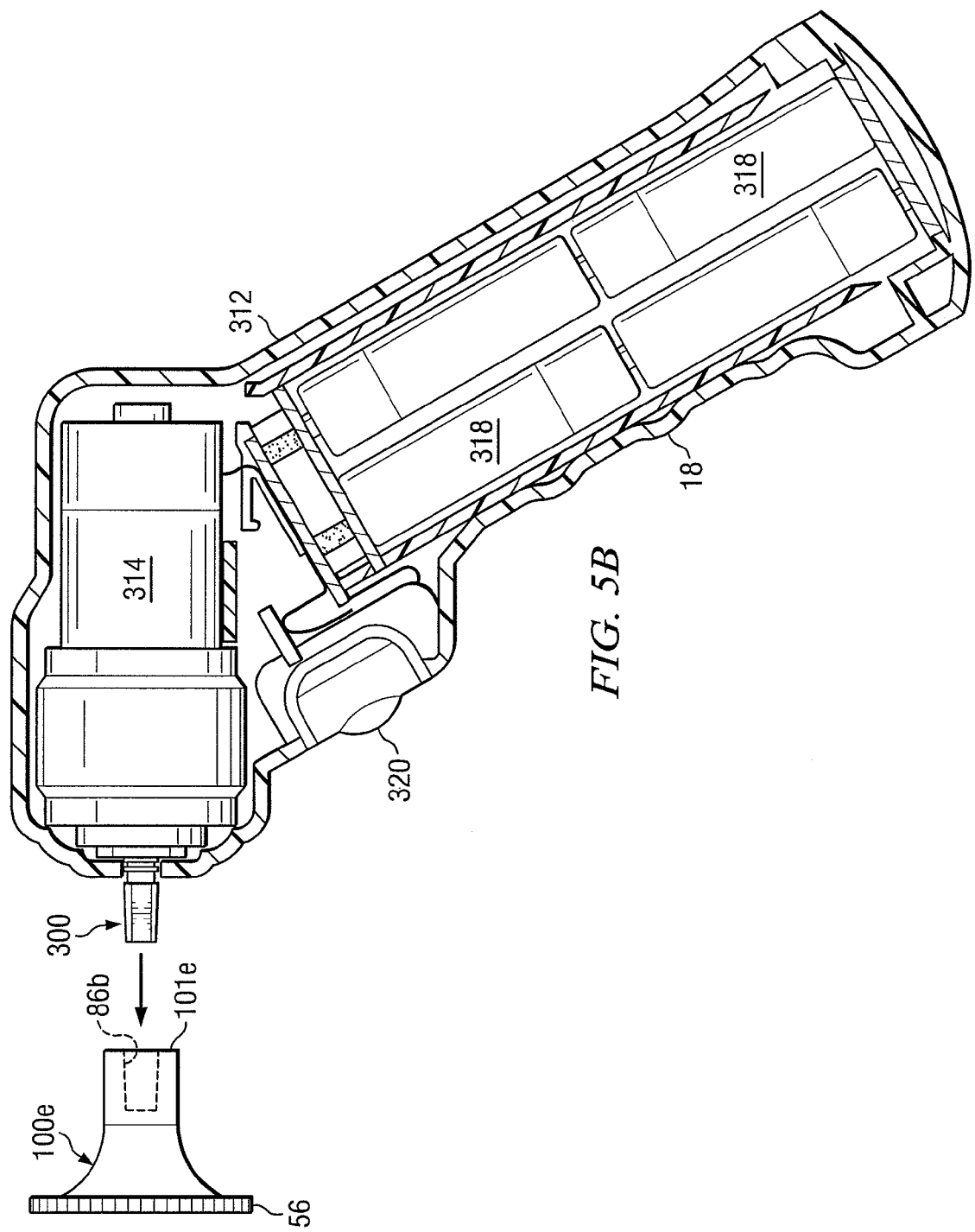
FIG. 5B shows an example illustration of a power driven apparatus operable for penetrating bone marrow of a bone and compatible with operating an auxiliary device.

FIG. 1D opening 186 may be formed in first end 181 to receive associated drive shaft 16a. See FIG. 1D. Opening 186 may be formed with various configurations and/or dimensions. For some applications opening 186 may include a passageway or channel sized to receive portions of drive shaft 16a. One or more webs 136 may be formed in end 181 extending from opening 186. Open segments or void spaces 138 may be formed between webs 136. Respective projections 146 extending from adjacent portions of handle 12a may be releasably engaged with webs 136 and void spaces 138. Opening 186 and associated web 136 may be used to releasably couple connector 180 with either a manual driver or a powered driver. An example of a powered driver is shown in FIG. 5B.

FIG. 1E shows an enlarged view of penetrator assembly 160.

As shown in FIG. 1F, penetrator assembly 160 may include connector 180, hub and associated hub 200, outer penetrator 210 and inner penetrator 220. Penetrator assembly 160 may include an outer penetrator such as a cannula, hollow tube or hollow drill bit and an inner penetrator such as a stylet or trocar. Various types of stylets and/or trocars may be disposed within an outer penetrator. For some applications outer penetrator or cannula 210 may be described as a generally elongated tube sized to receive inner penetrator or stylet 220 therein. Portions of inner penetrator 220 may be disposed within longitudinal passageway 184 extending through outer penetrator 210. The outside diameter of inner penetrator 220 and the inside diameter of longitudinal passageway 184 may be selected such that inner penetrator 220 may be slidably disposed within outer penetrator 210.

Metal disc 70 may be disposed within opening 186 for use in releasably attaching connector 180 with a magnetic drive shaft. For some applications, drive shaft 16a may be magnetized. End 223 of inner penetrator 220 is preferably spaced from metal disc 70 with insulating or electrically nonconductive material disposed therebetween.

Tip 211 of outer penetrator 210 and/or tip 222 of inner penetrator 220 may be operable to penetrate bone and associated bone marrow. The configuration of tips 211 and/or 222 may be selected to penetrate a bone or other body cavities with minimal trauma. First end or tip 222 of inner penetrator 220 may be trapezoid shaped and may include one or more cutting surfaces. In one embodiment outer penetrator 210 and inner penetrator 220 may be ground together as one unit during an associated manufacturing process. Providing a matching fit allows respective tips 211 and 222 to act as a single drilling unit which facilitates insertion and minimizes damage as portions of penetrator assembly 160 are inserted into a bone and associated bone marrow. Inner penetrator 220 may also include a longitudinal groove (not expressly shown) that runs along the side of inner penetrator 220 to allow bone chips and/or tissues to exit an insertion site as penetrator assembly 160 is drilled deeper into an associated bone. Outer penetrator 210 may be formed from stainless steel, titanium or other materials of suitable strength and durability to penetrate bone.

Hub 200 may be used to stabilize penetrator assembly 160 during insertion of an associated penetrator into a patient's skin, soft tissue and adjacent bone at a selected insertion site. First end 201 of hub 200 may be operable for releasable engagement or attachment with associated connector 180. Second end 202 of hub 200 may have a size and configuration compatible with an associated insertion site for outer penetrator 210. The combination of hub 200 with outer penetrator 210 may sometimes be referred to as a "penetrator set" or intraosseous needle.

For some applications connector 180 may be described as a generally cylindrical tube defined in part by first end 181 and second end 182. The exterior of connector 180 may include an enlarged tapered portion adjacent to end 181. A plurality of longitudinal ridges 190 may be formed on the exterior of connector 180 to allow an operator to grasp associated penetrator assembly 160 during attachment with a drive shaft. See FIG. 1E. Longitudinal ridges 190 also allow connector 180 to be grasped for disengagement from hub 200 when outer penetrator 210 has been inserted into a bone and associated bone marrow.

Second end 182 of connector 180 may include opening 185 sized to receive first end 201 of hub 200 therein. Threads 188 may be formed in opening 185 adjacent to second end 182 of connector 180. Threaded fitting 188 may be used in releasably attaching connector 180 with threaded fitting 208 adjacent to first end 201 of hub 200.

First end 201 of hub 200 may include a threaded connector 208 or other suitable fittings formed on the exterior thereof. First end 201 may have a generally cylindrical pin type configuration compatible with releasably engaging second end or box end 182 of connector 180.

For some applications end 202 of hub 200 may have the general configuration of flange. Angular slot or groove 204 sized to receive one end of protective cover or needle cap 234 may be formed in end 202. Slot or groove 204 may be used to releasable engage cover 234 with penetrator assembly 160. See FIGS. 1A, 1E and 2. For some applications cover 234 may be described as a generally hollow tube having rounded end 232. Cover 234 may be disposed within associated slot 204 to protect portions of outer penetrator 210 and inner penetrator 220 prior to attachment with an associated handle. Cover 234 may include a plurality of longitudinal ridges 236 formed on the exterior thereof. Longitudinal ridges 236 cooperate with each other to allow installing and removing cover or needle cap 234 without contaminating portions of an associated penetrator. Cover 234 may be formed from various plastics and/or metals.

The dimensions and configuration of second end 202 of hub 200 may be varied to accommodate various insertion sites and/or patients. Hub 200 may be satisfactorily used with a wide variety of flanges or other configurations compatible for contacting a patient's skin. Also, end 202 and associated flange may be used with a wide variety of hubs.

The present invention is not limited to hub 200, end 202 or the associated flange. Passageway 206 may extend from first end 201 through second end 202. The inside diameter of passageway 206 may be selected to securely engage the outside diameter of penetrator 210. The dimensions and configuration of passageway 206 may be selected to maintain an associated penetrator assembly engaged with hub 200.

FIG. 1G shows an enlarged view of tip 222 formed on the end of inner penetrator 220 disposed within outer penetrator 210. FIG. 1H shows an enlarged view of tip 211 formed on the end of outer penetrator 210.

In one embodiment of the invention steps for penetrating into bone marrow may include turning or rotating a drive shaft to insert penetrator 24 (See FIG. 4A), penetrator 110 (See FIG. 4B) or penetrator 210 (See FIG. 1A-1B) into a bone and associated bone marrow using rotational motion, disengaging an associated drive shaft from connector 80 or 180 and disengaging connector 80 or 180 from associated hub 100 or 200 leaving hub 100 or 200 and attached penetrator 24, penetrator 110 or penetrator 210 disposed in the bone marrow. The depth of penetration into a bone and associated bone marrow may be determined by the distance between second end 102 of hub 100 and the extreme end of tip 30 or tip 111 or the distance between second end 202 of hub 200 and the extreme end of tip 211. For some applications, threaded connection or fittings 108 or 208 may allow attachment with various types of Luer locks and/or Luer fittings associated with of intravenous tubing or a syringe with first end 101 of hub 100 or first end 201 of hub 200.

FIG. 1I shows outer penetrator or cannula 110 inserted into bone 130 and associated bone marrow 140. Various types of connections may be used to communicate fluids to bone marrow 140 via outer penetrator 210 may then be used to connect intravenous tubing 150 to outer penetrator 210. Right angle connector 132 has the advantage of allowing tubing 150 to be connected to outer penetrator 110 at an angle that will not kink or pinch off the lumen of tubing 150. Lock nut 133 may be used to engage right angle connector 132 with hub 200.

FIG. 1I illustrates only one example of a connector that may be used to communicate fluids between outer penetrator 110 and tubing 150. Intravenous tubing may be used to provide intravenous fluids and/or medications to associated bone marrow. The tubing may also be used in withdrawing a sample of blood from the bone marrow. Other connectors or adapters may also be used to connect a penetrator to an intravenous tubing, other types of tubing and/or a syringe. See FIG. 7.

Figure 3A:
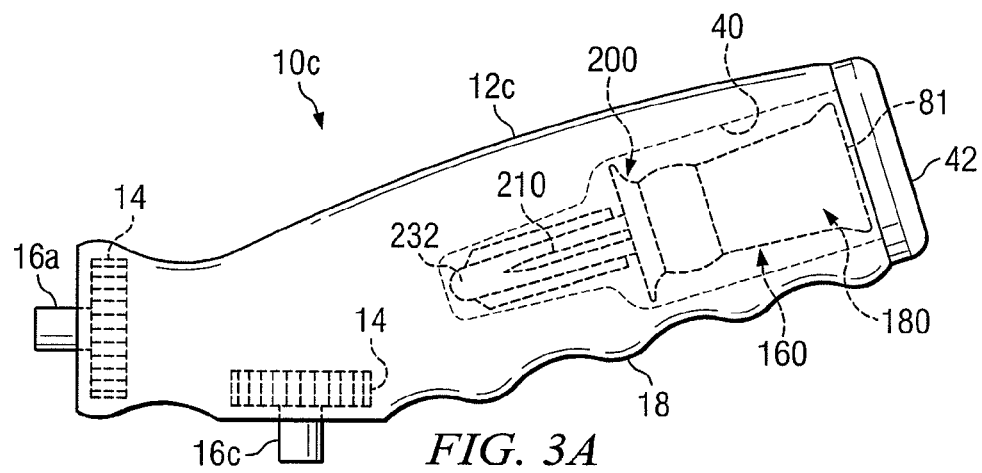
FIG. 3A shows an example illustration of an apparatus operable for penetrating bone marrow of a bone in accordance with teachings of the present invention.

Apparatus formed in accordance with teachings of the present invention may have ergonomic designs that allow insertion pressure or forces, for example, manual force, to be applied with relative ease and at the same time permit rotation action of an associated handle. In FIG. 3C drive shaft 16 with associated handle 12e may be aligned with an anatomically neutral position of an operator's hand and wrist as it pronates and suppinates. This alignment may allow better axial orientation of a penetrator assembly as an associated penetrator is inserted into a bone and associated bone marrow with less chance of excessive movement and/or misalignment of the penetrator which might result in undesired widening and/or elongation of an associated insertion hole. Insertion forces are not limited to rotation but may include reciprocal or direct axial forces applied by manual force.

Figure 2:
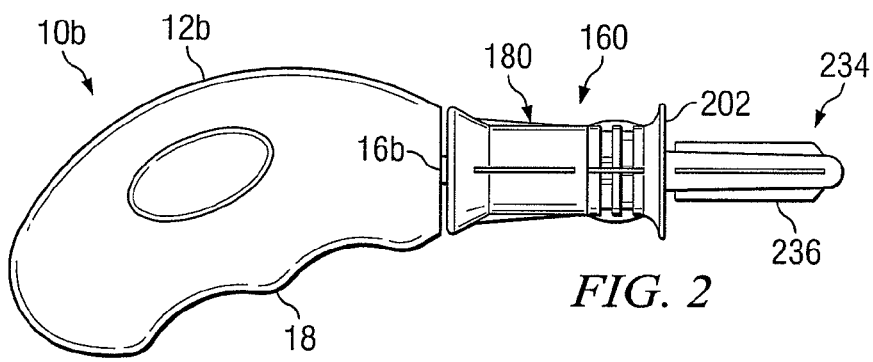
FIG. 2 shows an example illustration of an apparatus for penetrating bone marrow of a bone in accordance with teachings of the present invention.

FIG. 2 shows another example of apparatus which may be used to insert a penetrator into bone marrow in accordance with teachings of the present invention. FIG. 2 shows manual driver 10b wherein handle 12b includes drive shaft 16b. Manual driver 10b may also include an optional ratchet mechanism such as shown in FIG. 3A. Handle 12b may be releasably engaged with penetrator assembly 160 and for any other penetrator assembly incorporating teachings of the present invention.

Apparatus 10c as shown in FIG. 3A may also include first drive shaft 16a and second drive shaft 16c. Drive shafts 16a and 16c may include respective ratchet mechanisms 14. Drive shaft 16a and 16c may be disposed at different angles with respect to handle 12c to accommodate different insertion sites for an associated penetrator assembly and/or to accommodate different types of penetrator assemblies. Drive shafts 16a and 16c may have the same round shaped cross section or may have different cross sections.

For embodiments of the present invention such as shown in FIG. 3A, apparatus 10c may include handle 12c having at least one chamber 40 disposed therein. The configuration and size of chamber 40 (as shown in dotted lines in FIG. 3A) may be selected to accommodate one or more penetrator assemblies and/or other devices. Cap 42 may be secured on one end of handle 12c to retain a penetrator assembly or other device within chamber 40.

As discussed later in more detail, penetrator assemblies are preferably disposed within a sealed container prior to use. An example of one container incorporating teachings of the present invention is shown in FIG. 3D. Penetrator assembly 160 is shown in dotted lines in chamber 40 to indicate that various items other than container 43 may be satisfactorily disposed within a handle in accordance with teachings of the present invention. Chamber 40 may be configured to accommodate one or more containers 43 and/or multiple devices.

Figure 3B:
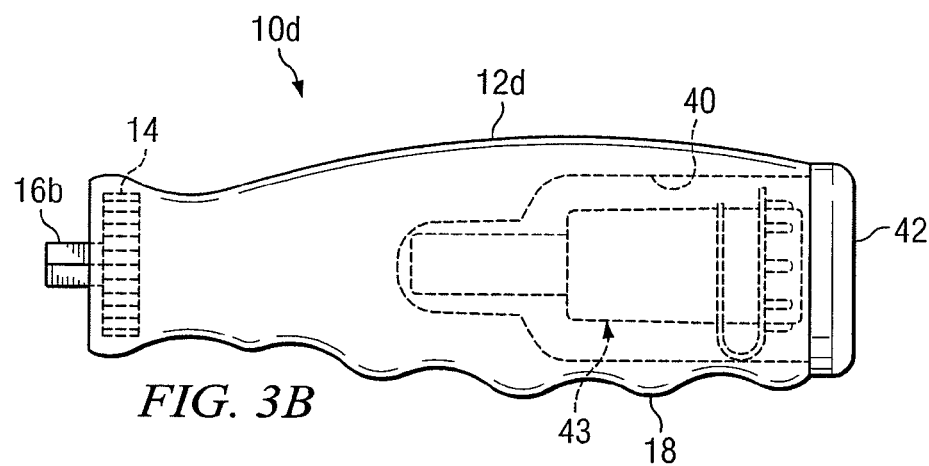
FIG. 3B shows an example illustration of an apparatus operable for penetrating bone marrow of a bone in accordance with teachings of the present invention.
Figure 3C:
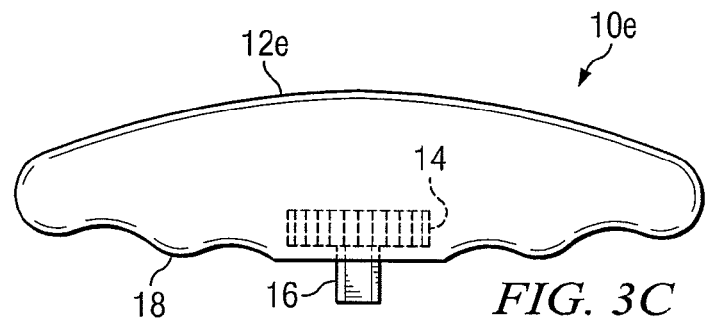
FIG. 3C shows an example illustration of an apparatus operable for penetrating bone marrow of a bone in accordance with teachings of the present invention.
Figure 3D:
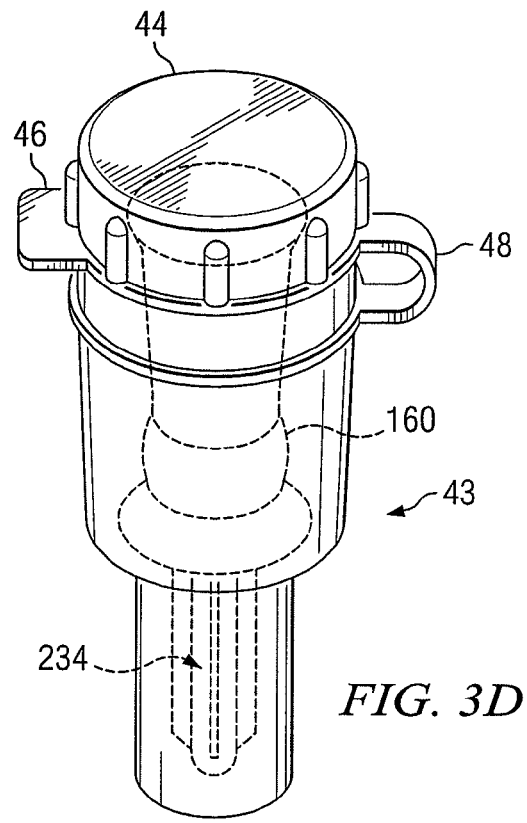
FIG. 3D is a schematic drawing showing an isometric view of a container operable to enclose a penetrator assembly in accordance with teachings of the present invention.

Apparatus 10d as shown in FIG. 3B may include handle 12d having a modified configuration as compared to previously described handles. Drive shaft 16b may have four sides which define a generally square or rectangular cross section. Drive shaft 16b may also have five (5) sides, six (6) sides or a key shape. Handle 12d also includes chamber 40 with container 43 disposed therein. As previously noted, apparatus 10e as shown in FIG. 3C may include generally T-shaped handle 12e.

As shown in FIG. 3D, container 43 includes an attached lid 44. Lid 44 includes tab 46 configured to be flipped open with one or more digits of the hand. Lid 44 of container 43 may be opened with one hand of an operator. With lid 44 open, an operator may engage a penetrator assembly with a drive shaft of either a manual or powered driver held in the other hand of the operator. Flexible strap 48 may be used to releasably engage lid 44 with container 43. A container incorporating teachings of the present invention allows a penetrator assembly to be retained in a sterile environment. When use of the penetrator assembly is required, a manual or powered driver may be engaged with a penetrator assembly incorporating teachings of the present invention without contaminating the penetrator assembly. As discussed later in more detail various mechanisms such as magnets, o-rings and/or ball detents may be satisfactorily used to allow releasable engagement of a drive shaft with a penetrator assembly.

Ratchet mechanism 14 (See FIGS. 3A, 3B and 3C) is an optional component that may be included in some embodiments to provide additional leverage for insertion of an associated penetrator. For example, a ratchet may function by engaging a connector attached to a hub of a needle assembly when rotational power is applied in a clockwise direction. Ratchet mechanism 14 may be reversible such that an associated handle may be rotated in either a clockwise or counterclockwise direction. Apparatus incorporating teachings of the present invention may include a rotatable collar (not expressly shown) configured to lock and unlock a reversible ratchet mechanism in order to change the direction of rotation. Drive shafts incorporating teachings of the present invention may be connected to ratchet mechanism 14 to apply rotational force in only one direction. Ratchet mechanism 14 may be a "silent" type, including three ball bearings (not expressly shown) configured to produce a desired effect without accompanying noise produced by a conventional ratchet. Drive shafts may also be attached to handle incorporating teachings of the present invention (not expressly shown) without the use of ratchet mechanism 14.

Various types of penetrators and penetrator assemblies may be satisfactorily used with a handle incorporating teachings of the present invention. Examples of such penetrators and penetrator assemblies include, but are not limited to, penetrator assembly 22 as shown in FIG. 1A, penetrator assembly 22 as shown in FIG. 4A and penetrator assembly 60 as shown in FIG. 4B. For some applications penetrator assembly 22 may include connector 80, hub 100 and penetrator 24 as shown in FIG. 4A. For some applications penetrator assembly 60 may include connector 80, hub 100, cannula 110 and trocar 120 as shown in FIG. 4B. For some applications penetrator assembly 160 may include connector 180, hub 200, cannula 210 and trocar or stylet 220 as shown in FIG. 1A. Apparatus and methods incorporating teachings of the present invention may be used with a wide variety of handles, connectors, hubs and penetrators. The present invention is not limited to handles, connectors, flanges, penetrators and/or penetrator assemblies as shown in FIGS. 1A-6B. For some applications a handle or driver may be directly attached to a penetrator hub without the use of a connector.

For some applications a penetrator assembly may include only a single, hollow penetrator. For other applications a penetrator assembly may include an outer penetrator such as a cannula, hollow needle or hollow drill bit and an inner penetrator such as a stylet, trocar or other removable device disposed within the outer penetrator. Penetrator 24 is one example of a single, hollow penetrator. See FIG. 4A. Penetrator 24 may include one or more sideports (not expressly shown.) Cannulas 110 and 210 are examples of outer penetrators. Trocar 120 and stylet 220 are examples of an inner penetrator. See FIGS. 1B and 1E.

The size of a penetrator may vary depending upon the intended application for the associated penetrator assembly. Penetrators may be relatively small for pediatric patients, medium size for adults and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy. Some penetrators may be suitable for more than one purpose. The configuration and size of a penetrator may also vary depending upon the site chosen for insertion of each penetrator.

As shown in FIG. 4A, penetrator assembly 22 may include connector 80, hub and associated flange 100 and penetrator 24. For some applications penetrator 24 may be generally described as a hollow needle satisfactory for communicating fluids with bone marrow. Penetrator 24 may be configured to penetrate bone, bone marrow, or other tissues or cavities of a body. Various types of intraosseous needles and/or hollow drill bits may be used as penetrator 24. Tip 30 of penetrator 24 may be satisfactory for use in drilling a hole in a bone in response to rotation of handle 22. An opening (not expressly shown) may be formed in penetrator 24 approximate tip 30 to allow communication of fluids between a fluid flow passage (not expressly shown) formed in penetrator 24 and adjacent bone marrow.

As shown in FIGS. 4A and 4B, hub 100 may be used to stabilize a penetrator assembly during insertion of an associated penetrator through a patient's skin, soft tissue and adjacent bone at a selected insertion site. First end 101 of hub 100 may be operable for releasable engagement or attachment with associated connector 80. Second end 102 and associated flange of hub 100 may have a size and configuration compatible with an associated insertion site for penetrator 24. The combination of hub 100 with penetrator 24 may sometimes be referred to as "a penetrator set or assembly."

Various techniques may be satisfactorily used to releasably engage connector 80 with hub 100 and penetrator 24. For example, various types of mechanical fasteners including, but not limited to, mechanical fittings and threaded connections and/or Luer lock nuts may be satisfactorily used to releasably engage a handle with a penetrator in accordance with teachings of the present invention.

For some applications, connector 80 may be described as a generally cylindrical rod defined in part by first end 81 and second end 82. Longitudinal passageway 84 may extend from first end 81 through a portion of connector 80. For embodiments such as shown in FIG. 4B passage 84 preferably terminates prior to disc 70. For some applications longitudinal passageway 84 may be sized to receive a stylet or trocar. See FIG. 4B. For other applications connector 80 may be satisfactorily used without longitudinal passageway 84.

An enlarged opening may be formed in first end 81 to receive drive shaft 16. Threaded fitting 88 may be formed adjacent to second end 82 of connector 80 for use in releasably attaching connector 80 with first end 101 of hub 100. For some applications a plurality of ridges or indentations 90 may be formed on the exterior of connector 80 to allow an operator to grasp penetrator assembly 22 during attachment with drive shaft 16. Ridges or indentations 90 also allow connector 80 to be grasped for disengagement from hub 100 when penetrator 24 has been inserted into a bone and associated bone marrow.

For some applications end 102 of hub 100 may include an annular slot or groove 104 sized to receive one end of protective cover 32. Slot or groove 104 may be used to releasably engage cover 32 with penetrator assembly 22 and/or penetrator assembly 60. See FIG. 4B. For some applications cover 32 may be described as a generally hollow tube having rounded end 34. Cover 32 may be disposed within associated slot 104 to protect portions of a penetrator prior to attachment with a manual or power driver. Cover 32 may be formed from various plastics and/or metals and may be employed with alternate penetrator assembly embodiments.

The dimensions and configuration of second end 102 of hub 100 may be varied to accommodate various insertion sites and/or patients. Passageway 106 may extend from first end 101 through hub 100 to second end 102. The inside diameter of passageway 106 may be selected to securely engage the outside diameter of penetrator 24 and/or the outside diameter of cannula 110. The dimensions and configuration of passageway 106 may be selected to maintain an associated penetrator securely engaged with hub 100. Several techniques and methods may be used to secure a penetrator with a hub including, but not limited to, knurling, shot peening, flanges (not expressly shown) glue and/or serrations.

First end 101 of hub 100 may include threaded connection 108 or other suitable fitting on the exterior thereof. First end 101 may have a generally cylindrical pin type configuration compatible with releasably engaging second end or box end 82 of connector 80. Threaded connection 88 may be releasably engaged with threads 108.

Connectors 80, 80b, 80c and 80d may have similar exterior configurations and dimensions as respectively shown in FIGS. 4A, 4B, 4C and 4D. However, the dimensions and configurations of connectors incorporating teachings of the present invention may be substantially modified as compared to connectors 80, 80b, 80c and 80d.

Opening 86 in each connector 80 may have various configurations and dimensions for releasable engagement with an associated drive shaft. For some applications a drive shaft may have four sides, five sides, six sides, or eight sides. A drive shaft may also have a "D shaped" cross section. The drive shaft may also be round or any other keyed configuration. Drive shafts and associated openings in a connector may be tapered relative to each other (not expressly shown).

Drive shaft 16 as shown in FIG. 4A may have five sides. Corresponding opening 86b as shown in FIG. 4B may also include five sides compatible with releasably receiving drive shaft 16. For some applications, metallic disc 70 may be disposed within opening 86b opposite from end 81. Metallic disc 70 may be satisfactorily used to releasably engage penetrator assembly 60 as shown in FIG. 4B with a drive shaft formed from materials which are magnetized. Drive shaft 16 may include or incorporate a magnet configured to releasably engage metallic disc 70 disposed within penetrator assembly 60. Cooperation between metallic disc 70 and magnetized drive shaft 16 allows removing a penetrator assembly from a container such as container 43.

For other applications one or more magnets 72 and 74 may be disposed within the sides of opening 86 to releasably engage an associated drive shaft with connector 80b. Magnets 72 and 74 are shown in dotted lines in FIG. 1B. Magnets 72 and/or 74 may be used to releasably engage a connector with a drive shaft formed from appropriate metal alloys or other materials.

Figure 4C:
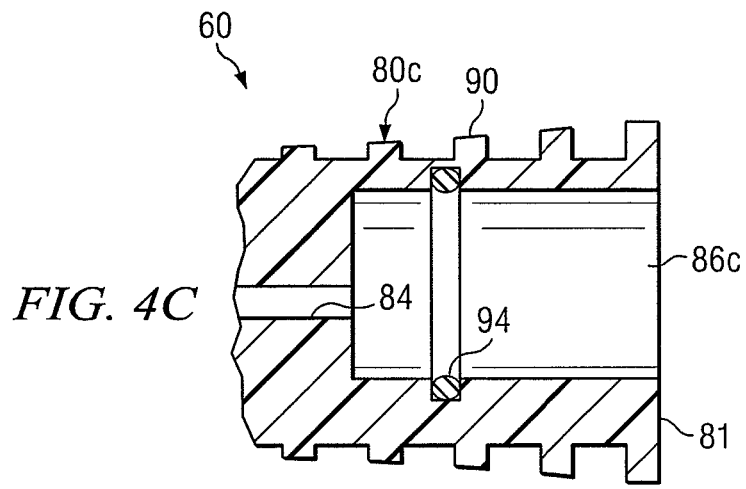
FIG. 4C is a schematic drawing in section with portions broken away showing another example of an opening formed in a penetrator assembly which may be releasably engaged with a drive shaft in accordance with teachings of the present invention.

For embodiments of the present invention such as shown in FIG. 4C, opening 86c may have a generally circular shaped cross section. O-ring 96 may be disposed within opening 86c of connector 80c. O-ring 96 may form a satisfactory engagement with an associated drive shaft having a corresponding generally circular cross section. Drive shafts 16a and 16c as shown in FIG. 3A may have a generally circular cross section.

Figure 4D:
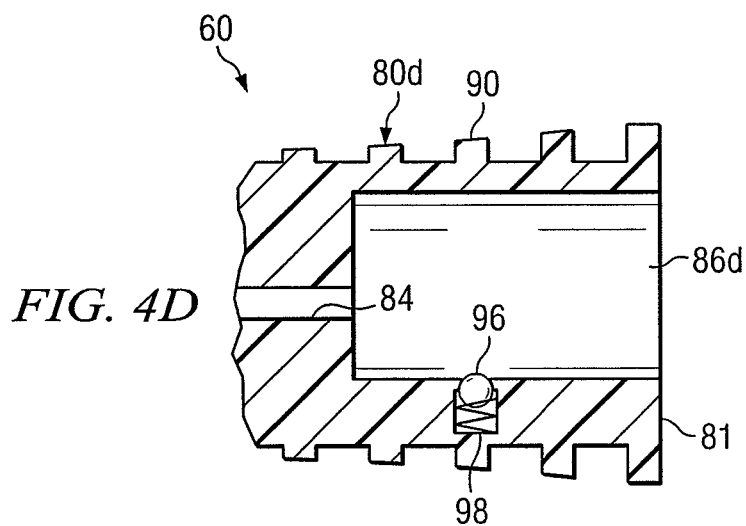
FIG. 4D is a schematic drawing in section with portions broken away showing still another example of an opening formed in a penetrator assembly which may be releasably engaged with a drive shaft in accordance with teachings of the present invention.

Connector 80d as shown in FIG. 4D may include ball 96 and spring 98 which engage a corresponding detent or recess (not expressly shown) in a drive shaft. Ball detent mechanism 96 and spring 98 may cooperate with each other to releasably engage connector 80d and associated penetrator assembly with a drive shaft. Other mechanisms may also be satisfactorily used to releasably engage a drive shaft with a connector in accordance with teachings of the present invention. Such mechanisms include but are not limited to snap ring connectors (not expressly shown), lock and key connectors (not expressly shown), and similar releasable connections.

For embodiments such as shown in FIG. 4B, various types of threaded connections or other suitable fittings may be used. End 82 of connector 80 preferably includes an enlarged opening or passageway sized to receive first end 101 of hub 100. Threads 88 formed within end 82 may be releasably engaged with threads 108 formed on the exterior of end 101.

For embodiments of the present invention such as shown in FIG. 4B, penetrator assembly 60 may include an outer penetrator such as a cannula, hollow needle or hollow drill bit and an inner penetrator such as a stylet or trocar. Various types of stylets and/or trocars may be disposed within an outer penetrator. For some applications, outer penetrator or cannula 110 may be described as having a generally elongated, hollow tube sized to receive inner penetrator or trocar 120 therein. Portions of trocar 120 may be disposed within longitudinal passageway 84 extending through connector 80. The outside diameter of trocar 120 and the inside diameter of longitudinal passageway 84 may be selected such that trocar 120 may be securely engaged with connector 80. For some applications, metallic disk 70 may be disposed within opening 86 adjacent to trocar 120.

Tip 111 of outer penetrator 110 and/or tip 112 of inner penetrator 120 may be operable to penetrate bone and associated bone marrow. The configuration of tips 111 and/or 121 may be selected to penetrate a bone or other body cavities with minimal trauma. First end or tip 121 of trocar 120 may include one or more cutting surfaces. In one embodiment outer penetrator 110 and inner penetrator 120 may be ground separately during the manufacturing process and later aligned to ensure an exact fit to allow respective tips 111 and 121 act as a single drilling unit to facilitate insertion and minimize damage as portions of penetrator assembly 60 are inserted into a bone and associated marrow. The resulting configuration of tips 111 and 121 may be formed to penetrate a bone or other body cavities with minimal trauma.

Inner penetrator 120 may also include a longitudinal groove (not expressly shown) that runs along the side of inner penetrator 120 to allow bone chips and/or tissue to exit an insertion site as penetrator assembly 60 is drilled deeper into an associated bone. Cannula 110 may be formed from stainless steel, titanium or other materials of suitable strength and durability to penetrate bone.

A wide variety of accessory tools and devices are frequently carried by emergency medical service personnel and/or first responders. Ring cutter 50 as shown in FIG. 5A may be representative of such accessory tools. Ring cutter 50 may include thumb lever 52 and finger protector 54. Ring cutting blade 56 may be rotatably mounted on arm 58 extending from handle 12f.

For some applications, ring cutting blade 56 may be engaged with a hub incorporating teachings of the present invention. For example, ring cutting blade 56 may be securely engaged with hub 100b such as shown in FIG. 5B. First end 101 of hub 110b may be modified to have opening 86b similar to opening 86b as described with respect to connector 80b. For some applications, handles 12, 12a, 12b, 12c, 12d and/or 12e may be releasably engaged with hub or hub 100b for use in rotating ring cutting blade 56. For other applications, power driven driver 312 may be attached with hub or hub 100b. Driver 312 may include electrical motor 314 coupled with drive shaft 300. Batteries or power supply 318 may be disposed within powered driver 312. Trigger 320 may be used to activate motor 314.

Examples of power drivers which may be used with a hub or flange are shown in U.S. Pat. No. 6,183,442 entitled "Tissue Penetrating Device and Methods of Using Same" and U.S. Pat. No. 5,554,154 entitled "Intra-Osseous Needle Drill." Power drivers are also shown in pending U.S. patent application Ser. No. 10/449,503 entitled "Apparatus and Method to Provide Emergency Access to Bone Marrow" filed May 30, 2003 and Ser. No. 10/449,476 entitled "Apparatus and Method to Access Bone Marrow" filed May 30, 2003.

Having a reliable powered driver may be of benefit to an operator in other situations requiring rotational forces or power. For example, drive shaft 300 may be mated to a variety of auxiliary devices that may be powered by rotational or reciprocal motion. Other examples of accessory or auxiliary devices (not expressly shown) which may be attached with a handle in accordance with teachings of the present invention include, but are not limited to, orthopedic fixation devices, portable suction devices, flashlights or any other medical or field device that uses a power source. Flashlight attachments to either a manual or powered driver may include a red light for night vision purposes or a white light (not expressly shown). Such lights may be of the LED type.

FIGS. 1A, 2, 3A-3C, 6A and 6B and 1B show embodiments of the present invention which include a manual driver which may be releasably engaged with a hub in accordance with the teachings of the present invention. Apparatus 10f as shown in FIG. 6A may include handle 12f with connector 280 formed as an integral component thereof. Various types of threaded connections and/or other fittings may be satisfactorily used to releasably engage driver 10f with hub 200. For some applications, threaded connection 188 may be formed within connector 280 for releasable engagement with threaded connection 208 formed on hub 200. In FIG. 6A, apparatus 10f may include penetrator or trocar 220 extending from handle 12f.

FIG. 6B shows apparatus 10g which includes handle 12g and hub 200. For embodiments of the present invention such as shown in FIG. 6B, apparatus 10g does not include a penetrator or trocar. Hub 200 may include previously described penetrator 24 with sideport or opening 26 formed therein.

FIG. 7 is a schematic drawing showing one example of a Luer type fitting or Luer type connection which may be satisfactorily formed between hub 200 and an intravenous tubing 150. Male fitting 40 may be inserted into one end of tubing 150. Male fitting 40 preferably includes tapered surface 62 designed to form a fluid tight seal with tapered surface 64 formed with hub 200 adjacent to end 210. Tapered surfaces 62 and 64 cooperate with each to form portions of a fluid tight Luer fitting or connection. Luer locking nut or luer collar 133 may be used to securely engage tapered surface 62 and 64 with each other. Luer locking nut 133 may be securely engaged with threads 208 formed on the exterior of hub 200 adjacent to end 201. After hub 200 and associated penetrator 210 have been disposed at a selected insertion site, male type Luer fitting 36 may be slideably disposed in female type Luer fitting 38. Luer fittings 36 and 38 preferably have tapered surfaces which engage with each other to form a substantially fluid tight seal between each other. Luer lock 133 may be used to securely engage to retain secure engagement between Luer fittings 36 and 38.

Although the present invention and its advantages have been described in detail, it should be understood that various changes, substitutions and alternations can be made herein without departing from the spirit and scope of the invention as defined by the following claims.

What is claimed is:

1. A method of accessing bone marrow of a bone comprising:
    inserting a penetrator, defined in part by an outer cannula and an inner trocar, into the bone and associated bone marrow by a handle rotating a drive shaft and an attached connector, the connector releasably attached to a hub that is attached to the outer cannula, the hub defining a flange with a maximum transverse dimension that is greater than a maximum transverse dimension of the connector, the flange configured to contact skin adjacent the bone when the penetrator is inserted into a patient's bone, wherein the hub is attached to the outer cannula at least at a point along the flange;
    detaching the handle and connector from the hub while the outer cannula is disposed in the bone and associated bone marrow; and
    removing the trocar from the cannula to allow access to the bone marrow through the cannula,
    wherein the flange is in fixed relation to a first end of the outer cannula, the first end of the outer cannula configured to be inserted into the bone and bone marrow,
    wherein the first end of the outer cannula has a first plurality of cutting surfaces,
    wherein an end of the inner trocar proximate to the first end of the outer cannula comprises a second plurality of cutting surfaces,
    wherein the first plurality of cutting surfaces and the second plurality of cutting surfaces are configured to fit together to form a single drilling unit.

2. The method of claim 1,
    wherein the connector comprises a tapered portion,
    wherein the tapered portion is disposed on an exterior surface of the connector,
    wherein the tapered portion comprises a plurality of longitudinal ridges.

3. The method of claim 2, wherein the plurality of longitudinal ridges is configured to be grasped by a user to insert the penetrator into the bone and associated bone marrow.

4. The method of claim 3, wherein the plurality of longitudinal ridges is further configured to be grasped by the user to detach the connector from the hub.

5. A method of accessing bone marrow of a bone comprising:
    releasably attaching a connector, a hub, and a penetrator with a handle operable to rotate the connector, hub, and penetrator, the penetrator including an outer cannula attached to the hub, and the connector releasably coupled to the hub via a Luer fitting that includes male threads formed on the hub;
    rotating the handle to rotate the connector and the penetrator to insert the penetrator into the bone and associated bone marrow;
    detaching the handle and the connector from the outer cannula when one end of the outer cannula is located at a desired position within the bone marrow; and
    connecting a tubing with the outer cannula via the Luer fitting to communicate fluid between the tubing and the bone marrow,
    wherein the connector is attached to an inner trocar, wherein the Luer fitting is configured to position the inner trocar at a predetermined position relative to the outer cannula, wherein the end of the outer cannula configured to be located at the desired position within the bone marrow has a first plurality of cutting surfaces, wherein an end of the inner trocar proximate to the end of the outer cannula configured to be located at the desired position within the bone marrow comprises a second plurality of cutting surfaces, wherein the first plurality of cutting surfaces and the second plurality of cutting surfaces are configured to fit together to form a single drilling unit.

6. The method of claim 5, wherein each of the first plurality of cutting surfaces fits with a respective cutting surface of the second plurality of cutting surfaces when the inner trocar is positioned at the predetermined position relative to the outer cannula.

7. The method of claim 5,
wherein the connector comprises a tapered portion,
wherein the tapered portion is disposed on an exterior surface of the connector,
wherein the tapered portion comprises a plurality of longitudinal ridges.

8. The method of claim 7, wherein the plurality of longitudinal ridges is configured to be grasped by a user to insert the penetrator into the bone and associated bone marrow.

9. The method of claim 8, wherein the plurality of longitudinal ridges is further configured to be grasped by the user to detach the connector from the outer cannula.

* * * * *